United States Patent
Baastians et al.

(10) Patent No.: US 8,947,659 B1
(45) Date of Patent: *Feb. 3, 2015

(54) TIME CORRELATED SINGLE PHOTON COUNTING BY TIME TO DIGITAL CONVERSION

(71) Applicant: Optech Ventures, LLC, Torrance, CA (US)

(72) Inventors: Glenn Baastians, Torrance, CA (US); Hankins Stephen, Long Beach, CA (US); Jerald Alan Cole, Long Beach, CA (US)

(73) Assignee: Optech Ventures, LLC, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,959

(22) Filed: Feb. 26, 2013

(51) Int. Cl.
G01J 3/44 (2006.01)
H01L 31/107 (2006.01)
G01N 21/65 (2006.01)

(52) U.S. Cl.
CPC .............. *H01L 31/107* (2013.01); *G01N 21/65* (2013.01)
USPC ........................................................ 356/301

(58) Field of Classification Search
USPC .............................................. 356/301, 72–73
See application file for complete search history.

(56) References Cited

U.S. PATENT DOCUMENTS 8,072,595 B1 * 12/2011 Bastiaans et al. ............. 356/301

* cited by examiner

*Primary Examiner* — Abdullahi Nur
(74) *Attorney, Agent, or Firm* — Lawrence S. Cohen

(57) ABSTRACT

A time correlated single photon counting system having a time to digital converter triggered by a laser fire event detector and the reception of a single photon. The system may be used for chemical agent detection based on Rayleigh scattering using optical time domain reflectometry techniques. The system may also be used for Raman detection using frequency to time transformations.

20 Claims, 16 Drawing Sheets

TIME CORRELATED SINGLE PHOTON COUNTING BY TIME TO DIGITAL CONVERSION

STATEMENT REGARDING FEDERALLY SPONSORED RESEARCH OR DEVELOPMENT

Portions of the present disclosure are based on research performed under contract number FA8650-09-M-6945 from the U.S. Department of Defense. The Government may have certain rights in this patent.

BACKGROUND

1. Field

This disclosure relates to the field of detecting and recording low-level light signals with increased resolution and precision.

2. Description of Related Art

Time-correlated single photon counting, or TCSPC, is based on the detection of single photons of a periodic light signal, the measurement of the detection times, and the reconstruction of the waveform from the individual time measurements. TCSPC makes use of the fact that for low-level, high-repetition rate signals the light intensity is usually low enough that the probability to detect more than one photon in one signal period is negligible. For each pulse of source light, the delay of the first photon that is reflected or emitted is determined and recorded. For the periodic light signal, many photons will be detected at varying time intervals. These detections can then be constructed into a histogram representing the distribution of photon probability over time.

FIG. 1 depicts a time-correlated single photon counting system known in the art (see also The bh TCSPC Handbook, Becker & Hickl GmbH, Berlin, Germany, $2^{nd}$ Edition, 2006). In FIG. 1, a detector 18, typically a photo multiplier tube (PMT), delivers pulses for individual photons of the repetitive light signal that are emitted or reflected from a sample. A Constant Fraction Discriminator (CFD) 4 is used to trigger on the pulses from the detector. The CFD 4 triggers at a constant fraction of the pulse amplitude, thus avoiding pulse-height induced timing jitter. Typically, the CFD 4 triggers at the baseline transition of a re-shaped pulse, which is equivalent to constant fraction triggering.

A second CFD 2 is used to obtain a timing reference pulse from the light source used to illuminate the sample. The reference signal is usually generated by a photodiode, or, if nanosecond flashlamps are used as the light source, by a PMT operated at medium gain. The reference pulses may have some amplitude fluctuation or amplitude drift. The use of a CFD 2 in the reference channel prevents these fluctuations from causing timing jitter or timing drift.

The output pulses of the CFDs 2, 4 are used as start and stop pulses of a time-to-amplitude converter (TAC) 6. The TAC 6 generates an output signal proportional to the time between the start and the stop pulse. Conventional TACs use a switched current source charging a capacitor. The start pulse switches the current on, the stop pulse off. If the current in the start-stop interval is constant, the final voltage at the capacitor represents the time between start and stop. Conventional TACs can provide for the resolution of time differences of up to a few picoseconds.

The output voltage from the TAC 6 is sent through a Biased Amplifier (AMP) 10. The amplifier 10 has a variable gain and a variable offset. It is used to select a smaller time window within the full-scale conversion range of the TAC 6. The amplified TAC signal is fed to an Analog-to Digital Converter (ADC) 12. The output of the ADC is the digital equivalent of the photon detection time. For optimum operation, the ADC should work with an extremely high precision. Preferably, the ADC 12 resolves the amplified TAC signal into thousands of time channels that have the same width. Any non-uniformity of the channel width results in a systematic variation of the numbers of photons in the channels, creating noise or curve distortion.

The ADC 12 output is used as an address word for a measurement data memory 14. When a photon is detected, the ADC 12 output word addresses a memory location corresponding to the time of the photon. By incrementing the data contents of the addressed location using the Adder 16, a histogram of the photon distribution over time is created.

Additional details regarding prior art time correlated single photon counting systems may be found in U.S. Pat. No. 6,342,701, "Time correlated photon counting," to Kash, dated Jan. 29, 2002; U.S. Pat. No. 6,596,980, "Method and apparatus to measure statistical variation of electrical signal phase in integrated circuits using time-correlated photon counting," to Rusu, et al., dated Jul. 22, 2003; and The bh TCSPC Handbook, Becker & Hickl GmbH, Berlin, Germany, $2^{nd}$ Edition, 2006.

U.S. Pat. No. 7,593,098, "High Dynamic Range Photon-Counting OTDR," to Brendel, dated Sep. 22, 2009 describes the operation of an optical time domain reflectometer in a gated mode. In Brendel, a gate width circuit is used to control the time during which a photodetector is activated. A position circuit is used to position the activation of the gate to allow a specific position in the fiber under analysis to be observed. Brendel discloses that the gate widths and positions are under the control of an operator to allow for controllable observation of specific positions of a fiber and to allow for finer observations of selected portions of the fiber. Brendel also discloses the use of an optical attenuator to avoid saturation of the photodetector. Even though saturation of the photodetector is avoided, Brendel discloses the operation of the photodetector in a manner in which multiple photons are detected to allow for diagnosis of the fiber under test.

SUMMARY

Described herein are devices, apparatus, methods, arrays, and systems for time correlated single photon counting and incorporating time correlated single photon counting.

Implementation of the present invention includes a system for time-correlated photon counting comprising: a delay generator configured to receive a trigger signal and configured to produce a delayed electrical output, wherein the delayed electrical output is based on a programmable delay; an event counter configured to receive the trigger signal and configured to produce an event output for each received trigger signal; a photon detector configured to receive light from a light source to be measured and configured to produce a detected photon signal upon reception of a photon; a gate pulse generator configured to receive the delayed electrical output and configured to provide a gate pulse to the photon detector for turning on the photon detector for reception of photons during the duration of the gate pulse; a time to digital converter configured to produce a time interval measurement based upon elapsed time between the trigger signal and the detected photon signal; and a host processor configured to receive the event output and the time interval measurement and configured to produce a history of time interval measurements. The programmable delay may comprise a plurality of sequentially increasing time delays with a time offset between each sequentially increasing time delay equal to a duration of the gate pulse, and the programmable delay increments from one time delay to a next time delay upon the reception of the trigger signal by the delay generator. The trigger signal may comprise an electrical output from a laser event detector, wherein the laser event detector produces the electrical output upon the detection of at least some portion of a laser pulse. The photon detector may comprise: a first avalanche photo diode configured to receive light from the light source to be measured and configured to produce a first avalanche photo diode electrical output; and a second avalanche photo diode masked from the light source to be measured and configured to produce a second avalanche photo diode electrical output, wherein both avalanche photo diodes are gated by the gate pulse and wherein the detected photon signal comprises a difference between the first avalanche photo diode electrical output and the second avalanche photo diode electrical output. The gate pulse may have a duration of 1 nanosecond or less. The time to digital converter may produce a time interval measurement having a resolution of 60 picoseconds or less. The time to digital converter may comprise a time to digital converter semiconductor device. The system may further comprise a delay processor commanding the delay generator to produce the programmable delay, wherein the delay processor commands a sequence of programmable delays to cover a time region of interest, and wherein the delay processor commands sufficient programmable delays with a same delay time to allow a desired signal to noise ratio to be achieved. The host processor and the delay processor may comprise a single processing system. The gate pulse may have a selectable variable duration.

Implementation of the present invention further includes a method for time-correlated photon counting from a light source comprising: generating sample event counts based on reception of trigger signals; generating a gate pulse based on the reception of each trigger signal, wherein the generation of the gate pulse is delayed by a programmable delay from the reception of each trigger signal; gating a photon detector with the gate pulse, wherein the photon detector provides an electrical output corresponding to a reception of one or more photons from the light source by the photon detector; measuring times starting from the reception of each trigger signal and ending with reception of each electrical output from the photon detector; and generating a table of time interval measurements based upon the measured times and the sample event counts, whereby the table of time interval measurements provides a histogram of photon counts versus time. The programmable delay may comprise a plurality of sequentially increasing time delays with a time offset between each sequentially increasing time delay equal to a duration of the gate pulse, and the programmable delay increments from one time delay to a next time delay upon the reception of the trigger signal. The reception of trigger signals may comprise detections of starts of laser pulses. The photon detector may comprise: a first avalanche photo diode configured to receive light from the light source to be measured and configured to produce a first avalanche photo diode electrical output; and a second avalanche photo diode masked from the light source to be measured and configured to produce a second avalanche photo diode electrical output, wherein both avalanche photo diodes are gated by the gate pulse and wherein the photon detector electrical output comprises a difference between the first avalanche photo diode electrical output and the second avalanche photo diode electrical output. The programmable delay may comprise a sequence of programmable delays that cover a time region of interest, and wherein gate pulses are generated with sufficient programmable delays with a same delay time to allow a desired signal to noise ratio to be achieved.

Implementation of the present invention still further includes a system for detection of chemical agents comprising: a laser producing laser pulses; a chemical sensing optical fiber configured to receive at least some portion of optical energy of the laser pulses; a laser event detector configured to receive some portion of the optical energy of the laser pulses and configured to produce a laser event detector electrical output; a delay generator configured to receive the laser event detector electrical output and configured to produce a delayed electrical output, wherein the delayed electrical output is based on a programmable delay; an event counter configured to receive the laser event detector electrical output and configured to produce an event output for each received laser event detector electrical output; a photon detector configured to receive Rayleigh backscattered light from the chemical sensing fiber and configured to produce a detected photon signal upon reception of a photon; a gate pulse generator configured to receive the delayed electrical output and configured to provide a gate pulse to the photon detector for turning on the photon detector for reception of photons during the duration of the gate pulse; a time to digital converter configured to produce a time interval measurement based upon elapsed time between the laser event detector electrical output and the detected photon signal; and a host processor configured to receive the event output and the time interval measurement and configured to produce a history of time interval measurements, whereby the history of time interval measurements correlates with the presence or absence of chemical agents at locations along the chemical sensing fiber. The programmable delay may comprise a plurality of sequentially increasing time delays with a time offset between each sequentially increasing time delay equal to a duration of the gate pulse, and the programmable delay increments from one time delay to a next time delay upon the reception of the laser event detector electrical output by the delay generator. The laser event detector may measure the energy of the laser pulses and may provide the energy measurements to the host processor. A variable optical attenuator may control the amount of optical energy directed to the photon detector. The photon detector may comprise: a first avalanche photo diode configured to receive the Rayleigh backscattered light and configured to produce a first avalanche photo diode electrical output; and a second avalanche photo diode masked from any light and configured to produce a second avalanche photo diode electrical output, wherein both avalanche photo diodes are gated by the gate pulse and wherein the detected photon signal comprises a difference between the first avalanche photo diode electrical output and the second avalanche photo diode electrical output.

Yet further implementation of the present invention includes a method for detection of chemical agents comprising: producing laser pulses; launching a portion of the energy of the laser pulses into chemical sensing fiber, wherein a light source comprises Rayleigh scattered light from the laser pulses launched into the chemical sensing fiber; detecting the start of each laser pulse, wherein the start of each laser pulse comprises a trigger signal; generating a sample event count based on reception of the trigger signal; generating a gate pulse based on the reception of the trigger signal, wherein the generation of the gate pulse is delayed by a programmable delay from the reception of the trigger signal; gating a photon detector with the gate pulse, wherein the photon detector provides an electrical output corresponding to a reception of one or more photons from the light source by the photon detector; measuring a time starting from the reception of the trigger signal and ending with reception of the electrical output from the photon detector; and generating a table of time interval measurements based upon measured times and sample event counts, whereby the table of time interval measurements provides a histogram of photon counts versus time and whereby the histogram correlates with the presence or absence of chemical agents at locations along the chemical sensing fiber. The programmable delay may comprise a plurality of sequentially increasing time delays with a time offset between each sequentially increasing time delay equal to a duration of the gate pulse, and the programmable delay increments from one time delay to a next time delay upon the reception of the trigger signal. The photon detector may comprise: a first avalanche photo diode configured to receive light from the light source to be measured and configured to produce a first avalanche photo diode electrical output; and a second avalanche photo diode masked from the light source to be measured and configured to produce a second avalanche photo diode electrical output, wherein both avalanche photo diodes are gated by the gate pulse and wherein the photon detector electrical output comprises a difference between the first avalanche photo diode electrical output and the second avalanche photo diode electrical output. The method may further comprise: measuring optical energy of each laser pulse; and, adjusting the histogram of photon counts based on the measured optical energy. The method may also comprise attenuating an optical energy level of the Rayleigh scattered light from the chemical sensing fiber.

Additional implementation of the present invention includes a system for Raman detection from a target comprising: a laser producing laser pulses; a first optical apparatus configured to direct at least some portion of optical energy of the laser pulses towards the target; a laser event detector configured to receive some portion of optical energy of the laser pulses and configured to produce a laser event detector electrical output; a wavelength dispersion apparatus having an input and an output; a second optical apparatus configured to receive some portion of Raman scattered light from the target and configured to direct the Raman scattered light to the wavelength dispersion apparatus input; a delay generator configured to receive the laser event detector electrical output and configured to produce a delayed electrical output, wherein the delayed electrical output is based on a programmable delay; an event counter configured to receive the laser event detector electrical output and configured to produce an event output for each received laser event detector electrical output; a photon detector coupled to the output of the wavelength dispersion apparatus and configured to produce a detected photon signal upon reception of a photon; a gate pulse generator configured to receive the delayed electrical output and configured to provide a gate pulse to the photon detector for turning on the photon detector for reception of photons during the duration of the gate pulse; a time to digital converter configured to produce a time interval measurement based upon elapsed time between the laser event detector electrical output and the detected photon signal; and a host processor configured to receive the event output and the time interval measurement and configured to produce a history of time interval measurements, whereby the history of time interval measurements correlates with a transformation of a Raman spectra to a time domain representation of the Raman spectra. The programmable delay may comprise a plurality of sequentially increasing time delays with a time offset between each sequentially increasing time delay equal to a duration of the gate pulse, and the programmable delay increments from one time delay to a next time delay upon the reception of the laser event detector electrical output by the delay generator. The photon detector may comprise: a first avalanche photo diode configured to receive the output of the wavelength dispersion apparatus and configured to produce a first avalanche photo diode electrical output; and a second avalanche photo diode masked from any light and configured to produce a second avalanche photo diode electrical output, wherein both avalanche photo diodes are gated by the gate pulse and wherein the detected photon signal comprises a difference between the first avalanche photo diode electrical output and the second avalanche photo diode electrical output. The second optical apparatus may comprise a large aperture telescope, whereby the system is deployable for stand-off detection of Raman scattering from a target. The wavelength dispersion apparatus may comprise a series of holographic filters. The wavelength dispersion apparatus may comprise optical fiber consisting of at least one of the following: single mode optical fiber, multi-mode optical fiber, photonic crystal fiber, or photonic bandgap fiber. The wavelength dispersion element may comprise a series of fiber Bragg gratings. The wavelength dispersion element may comprise an optical spectrograph. Principal component analysis of the time domain representation of the Raman spectra may provide identification of chemical substances.

Further implementation of the present invention includes a method for Raman scattering detection from a target comprising: producing laser pulses; launching a portion of the energy of the laser pulses towards a target; detecting the start of each laser pulse; generating a sample event count based on the detection of the start of each laser pulse; generating a gate pulse based on the detection of the start of each laser pulse, wherein the generation of the gate pulse is delayed by a programmable delay from the detection of the start of each laser pulse; receiving Raman scattered light from the target; dispersing the received Raman scattered light in time based on wavelengths of the Raman scattered light; gating a photon detector with the gate pulse, wherein the photon detector provides an electrical output corresponding to a reception by the photon detector of one or more photons from the time dispersed Raman scattered light; measuring a time starting from the detection of the start of each laser pulse and ending with reception of the electrical output from the photon detector; and generating a table of time interval measurements based upon measured times and sample event counts, whereby the table of time interval measurements provides a histogram of photon counts versus time and whereby the histogram correlates with a transformation of a Raman spectra to a time domain representation of the Raman spectra. The programmable delay may comprise a plurality of sequentially increasing time delays with a time offset between each sequentially increasing time delay equal to a duration of the gate pulse, and the programmable delay increments from one time delay to a next time delay upon detection of the start of each laser pulse. The photon detector may comprise: a first avalanche photo diode configured to receive light from the time dispersed Raman scattered light and configured to produce a first avalanche photo diode electrical output; and a second avalanche photo diode masked from the light source to be measured and configured to produce a second avalanche photo diode electrical output, wherein both avalanche photo diodes are gated by the gate pulse and wherein the photon detector electrical output comprises a difference between the first avalanche photo diode electrical output and the second avalanche photo diode electrical output. Receiving Raman scattered light from the target may comprise receiving the Raman scattered light with a large aperture telescope and the method comprises a method for stand-off detection of Raman scattering from the target. Dispersing the received Raman scattered light in time based on wavelengths of the Raman scattered light may comprise coupling the received Raman scattered light into a series of holographic filters. Dispersing the received Raman scattered light in time based on wavelengths of the Raman scattered light may comprise coupling the received Raman scattered light into an optical fiber having a series of fiber Bragg gratings. Dispersing the received Raman scattered light in time based on wavelengths of the Raman scattered light may comprise coupling the received Raman scattered light into an optical spectrograph. Dispersing the received Raman scattered light in time based on wavelengths of the Raman scattered light may comprise coupling the received Raman scattered light into optical fiber consisting of at least one of the following: single mode optical fiber, multi-mode optical fiber, photonic crystal fiber, or photonic bandgap fiber. The method may further comprise identifying chemical substances by applying principal component analysis to the time domain representation of the Raman spectra.

Further implementation of the present invention includes a single photon detector comprising: a first avalanche photo diode configured to receive light from a light source to be measured and configured to produce a first avalanche photo diode electrical output; and a second avalanche photo diode masked from the light source to be measured and configured to produce a second avalanche photo diode electrical output, wherein both avalanche photo diodes are gated by a gate pulse and wherein a photon detector electrical output comprises a difference between the first avalanche photo diode electrical output and the second avalanche photo diode electrical output. The detector may further comprise a comparator configured to receive the photon detector electrical output and configured to produce a detected photon output if the photon detector electrical output exceeds a selected threshold. The first avalanche photo diode and the second avalanche photo diode may comprise Geiger mode silicon avalanche photo diodes. The first avalanche photo diode and the second avalanche photo diode may be connected differentially and the gate pulse may be applied differentially to a cathode of the first avalanche photo diode and to an anode of the second avalanche photo diode. A reverse bias voltage may be applied to the first avalanche photo diode and the second avalanche photo diode at a voltage below a Geiger mode reverse bias voltage for the avalanche photo diodes. The detector may further comprise one or more thermo electric coolers, wherein the thermo electric coolers are configured to maintain the avalanche diodes at a selected temperature. The detector may further comprise one or more step recovery diodes electrically coupled to the gate pulse, wherein the step recovery diodes are configured to sharpen edges of the gate pulse.

Further implementation of the present invention includes a method for single photon detection comprising: receiving light from a light source to be measured at a first avalanche photo diode, wherein the first avalanche photo diode produces a first avalanche photo diode electrical output; masking light from a second avalanche photo diode, wherein the second avalanche photo diode produces a second avalanche photo diode electrical output; simultaneously gating on the first avalanche photo diode and the second avalanche photo diode for a selected time duration; and differentially comparing the first avalanche photo diode electrical output and the second avalanche photo diode electrical output to produce a photon detection electrical output. The method may further comprise: comparing the photon detection electrical output to a selected threshold; and outputting a detected photon signal if the photon detection electrical output exceeds the selected threshold. The first avalanche photo diode and the second avalanche photo diode may comprise Geiger mode silicon avalanche photo diodes. Simultaneously gating the avalanche photo diodes may comprise differentially gating the first avalanche photo diode and the second avalanche photo diode. The method may further comprise reverse biasing the first avalanche photo diode and the second avalanche photo diode at a voltage below a Geiger mode reverse bias voltage for the avalanche photo diodes. The method may further comprise sharpening edges of a gate pulse used to gate on the first avalanche photo diode and the second avalanche photo diode.

DETAILED DESCRIPTION

Exemplary embodiments of the present invention are more particularly described in the following examples that are intended as illustrative only since numerous modifications and variations therein may be apparent to those skilled in the art. As used in the specification and in the claims, "a," "an," and "the" can mean one or more, depending upon the context in which it is used. Several embodiments of the present invention are now described with reference to the figures, in which like numbers indicate like parts throughout the figures.

Time-Correlated Single Photon Counting Systems

Figure 1:
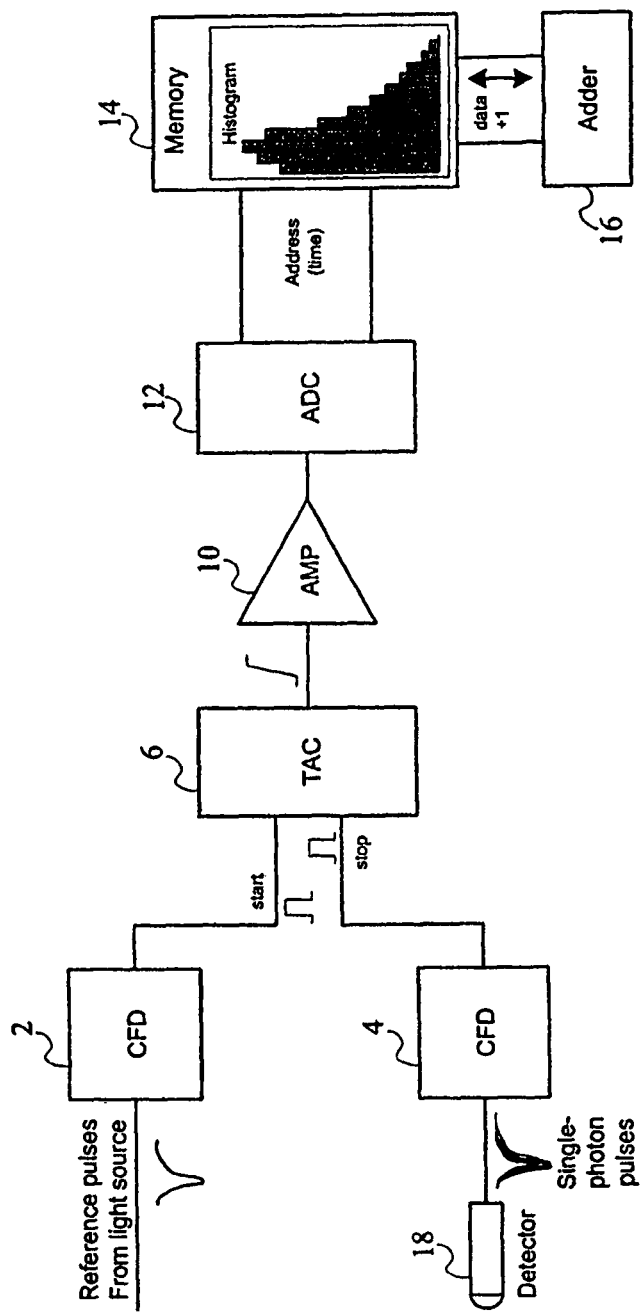
FIG. 1 (prior art) depicts a time-correlated single photon counting system.
Figure 2:
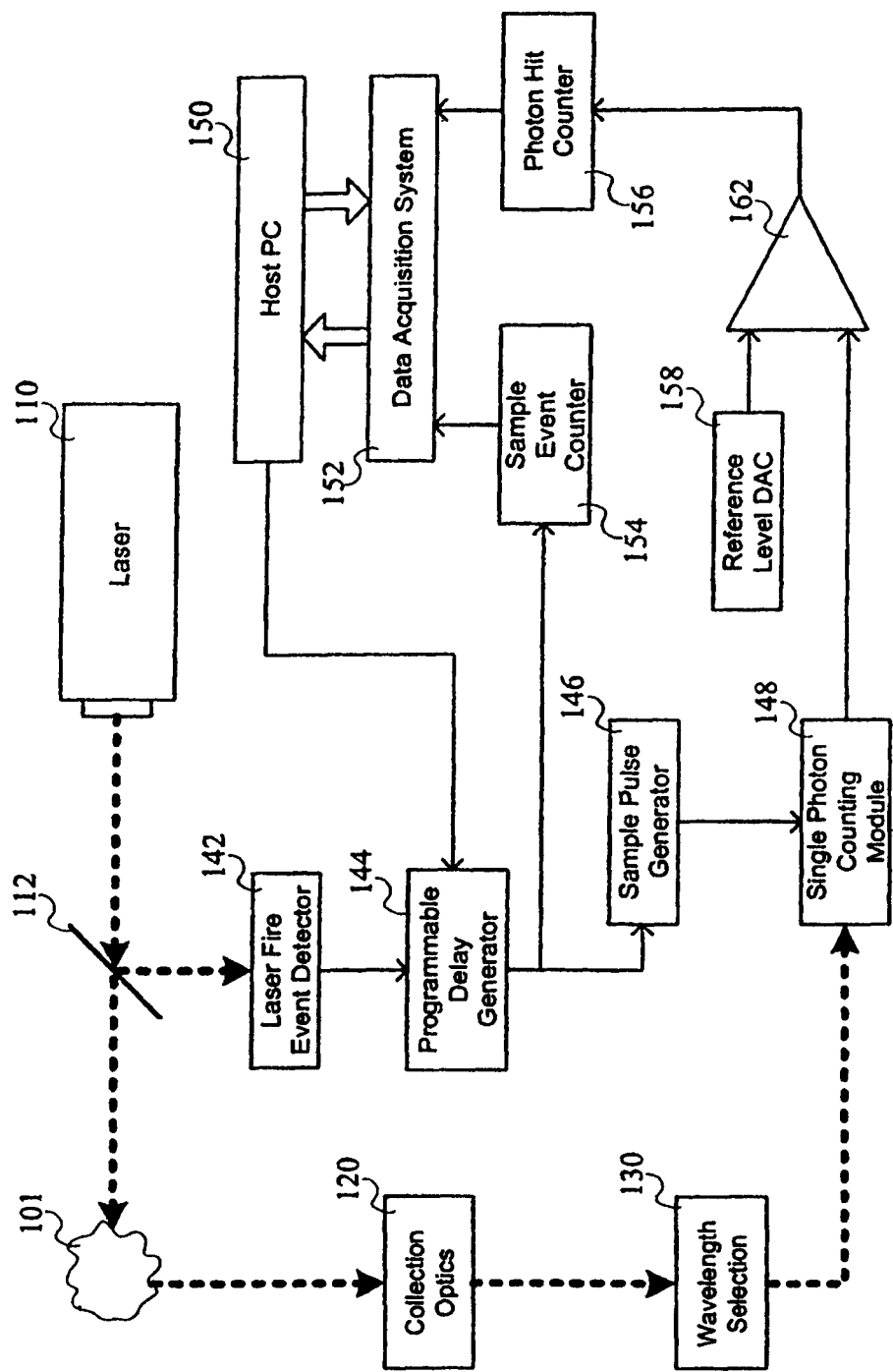
FIG. 2 depicts a time-correlated single photon counting system.

FIG. 2 depicts a time-correlated single photon counting system. In FIG. 2, a laser 110 fires pulses at a target 101 from which the system collects photons for counting. Such a system may be used for Rayleigh scattering detection or Raman scattering detection as described in detail below. Those skilled in the art will understand that the described time-correlated single photon counting system may have many applications.

Returning to FIG. 2, laser light pulses from the laser 110 are directed through a half-silvered mirror 112 to the target 101. Light pulses will then scatter from the target 101 and be collected by collection optics 120. The collection optics 120 operate to focus light scattering from the target 101 into optical fiber or other light conducting apparatus. The focused light may then be directed to a wavelength selection apparatus 130 that may be used to filter out light at the wavelength of the laser 110 and/or temporally separate light at different wavelengths, as discussed in further detail below.

In FIG. 2, each time the laser 110 fires a pulse, a portion of the laser light is directed by a partially-silvered mirror 112 to a laser fire event detector 142. The laser fire event detector 142 detects the start of each laser pulse from the laser 110. When the start of a laser pulse is detected, a logic signal is sent to a programmable delay generator 144. The programmable delay generator 144 sends out a signal that is delayed from the signal it receives. Preferably, the programmable delay generator is programmed to provide delays at 10 picosecond intervals or better.

The signal from the programmable delay generator 144 is sent to a sample event counter 154 and is used to trigger a sample pulse generator 146. The sample event counter 154 counts the number of detected laser pulses. The programmable delay generator delay setting is recorded by the host PC 150. The sample pulse generator 146 enables a single photon counting module 148 for the detection of a single photon from the wavelength selection apparatus 130. Preferably, the SPCM 148 is configured to only detect photons during the active time of the sample pulse generator 146. Preferably, the SPCM 148 rejects photons, to the highest extent possible, when the sample pulse is inactive, but counts photons with the greatest efficiently possible (i.e. quantum efficiency) when the sample pulse is active. The greater the amplitude of sample pulse generator 146, the greater the rejection of unwanted photon detect events when the sample pulse is inactive. The ability of the SPCM to reject the effects of high photon flux when the sample pulse is inactive ultimately determines the dynamic range of the overall operation of the system.

Figure 11A:
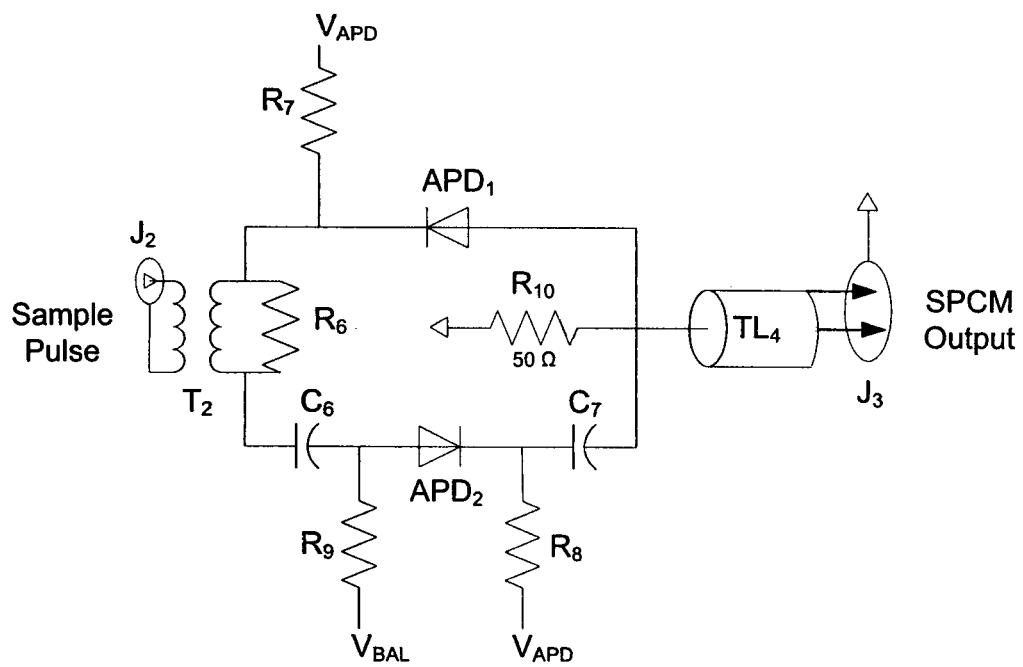
FIG. 11A shows a schematic diagram of a single photon counting module.
Figure 11B:
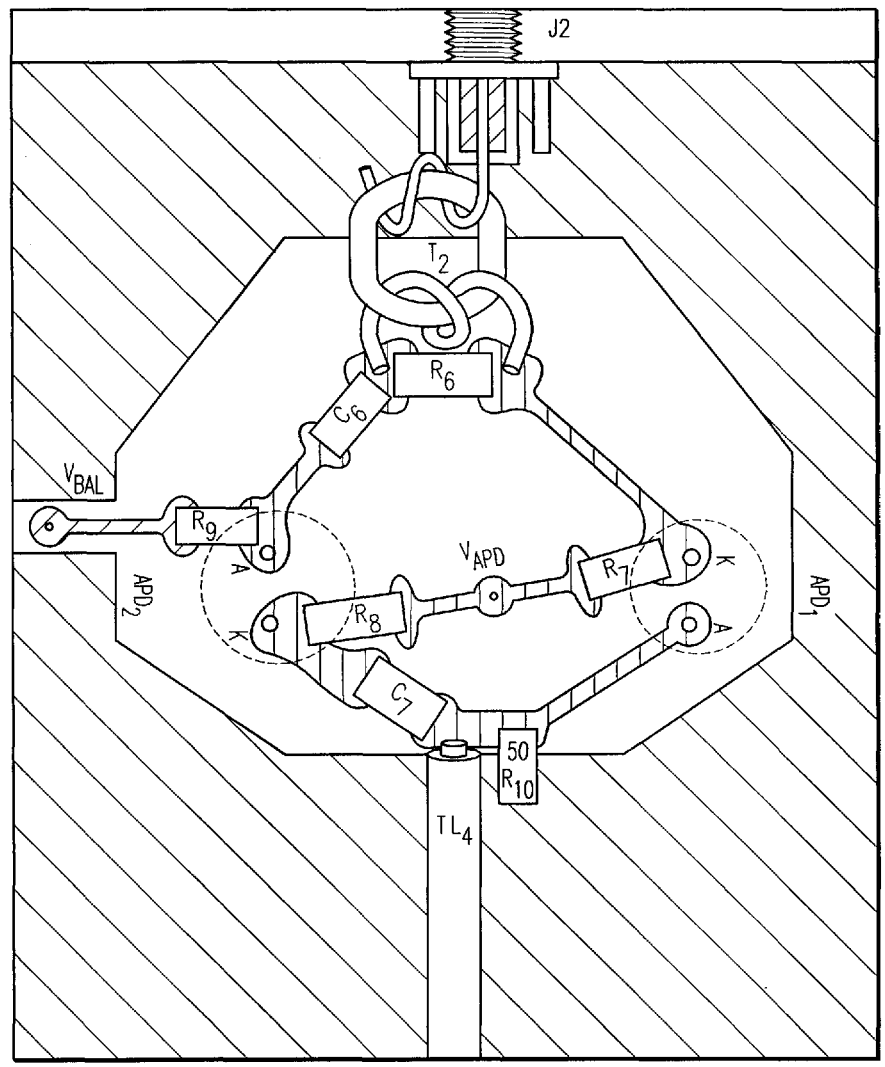
FIG. 11B shows a preferred layout of the components schematically depicted in FIG. 11A.

The single photon counting module (SPCM) 148 may comprise a pair of differentially connected avalanche photodiodes (APDs), as shown in FIGS. 11A and 11B, whose reverse bias is much less than what is necessary to permit a photon induced avalanche (30 volts or more away from the published Geiger operating voltage). One APD may be configured to receive light scattered from target 101 (through the collection optics 120 and wavelength selection apparatus 130, if applicable), while the other APD may be masked from light detection and so configured to provide an exact balance to the dynamic capacitance vs. reverse bias voltage characteristics of this class of APD. The better this balancing, the better the rejection of the high voltage sampling pulse, and the higher the sampling pulse can be applied to the APD pair. A photon induced avalanche on the exposed APD creates an imbalance pulse which is detected by comparator 162. The sample pulse generator 146 provides a sample pulse having the shortest practical period (the shorter the period, the greater the resolution) preferably, of 1 nanosecond period during which the SPCM 148 is enabled to detect a single photon. If a photon is seen within the sample pulse period, the SPCM 148 in combination with an amplifier 162 and a reference level digital-to-analog converter (DAC) 158 sends a signal to a photon hit counter 156. The reference level DAC 158 adjusts the level at which a photon is considered to be detected. Those skilled in the art will understand that the amplifier 162 and DAC 158 combination may serve as a comparator.

The sample event counter 154 and the photon hit counter 156 both send their data to the data acquisition system 152, which operates to place each photon hit in the appropriate time bin, as described below. The host PC 150 may be used to control the data acquisition system 152 and to provide further processing of the acquired data. The ratio between the photon hit counts and the sample event counts is the photon hit rate. If the photon hit rate is at 100% (i.e., a photon hit every time the SPCM 148 is sampled), a histogram of the photon distribution can not be effectively created because the SPCM is effectively saturated with too much light. Said differently, no information is derived from an SPCM which sees a photon every sample time. Obviously, no information is derived by an SPCM which is never triggered by a photon detect event. Hence, it is preferable to adjust input light level to the SPCM such that the photon hit ratio probability is somewhere between 10% and 90%. Further, in order to reduce the false photon detect events, the reference level DAC 158, should be adjusted sufficiently high to reject thermal-noise-induced weak avalanche events, but sufficiently low to permit the slightly higher amplitude photon-induced avalanche events to be output as a logic pulse from comparator 162.

Typically, programmable delay generator 144 is set for a specific delay setting and allowed to remain at that delay setting while a number of sample event counts from 154 and photon hit counts 156, are counted. The number of sample event counts at each delay setting determines the signal-to-noise ratio of the measurement. For example, 10,000 samples would be required to provide a SNR or 40 dB. After the required number of sample events have been counted and collected by the data acquisition system 152, the host PC increments the programmable delay generator 144 to the next setting and the process repeats.

In order to maintain high SNR and high resolution measurements, many samples should be counted at ever smaller programmable delay generator step sizes. Preferably, the host PC 150 scans the programmable delay generator 144 while continuously collecting samples from the event and hit counters 154, 156. Photons arriving at the SPCM 148 anytime during the sample pulse active time will be counted by the hit counter 156. For example, if the sample pulse were 1 ns wide, then all photons arriving at the SPCM 148 anytime during the sample pulse would be considered as arriving at the same time regardless of their actual arrival time.

Figure 3:
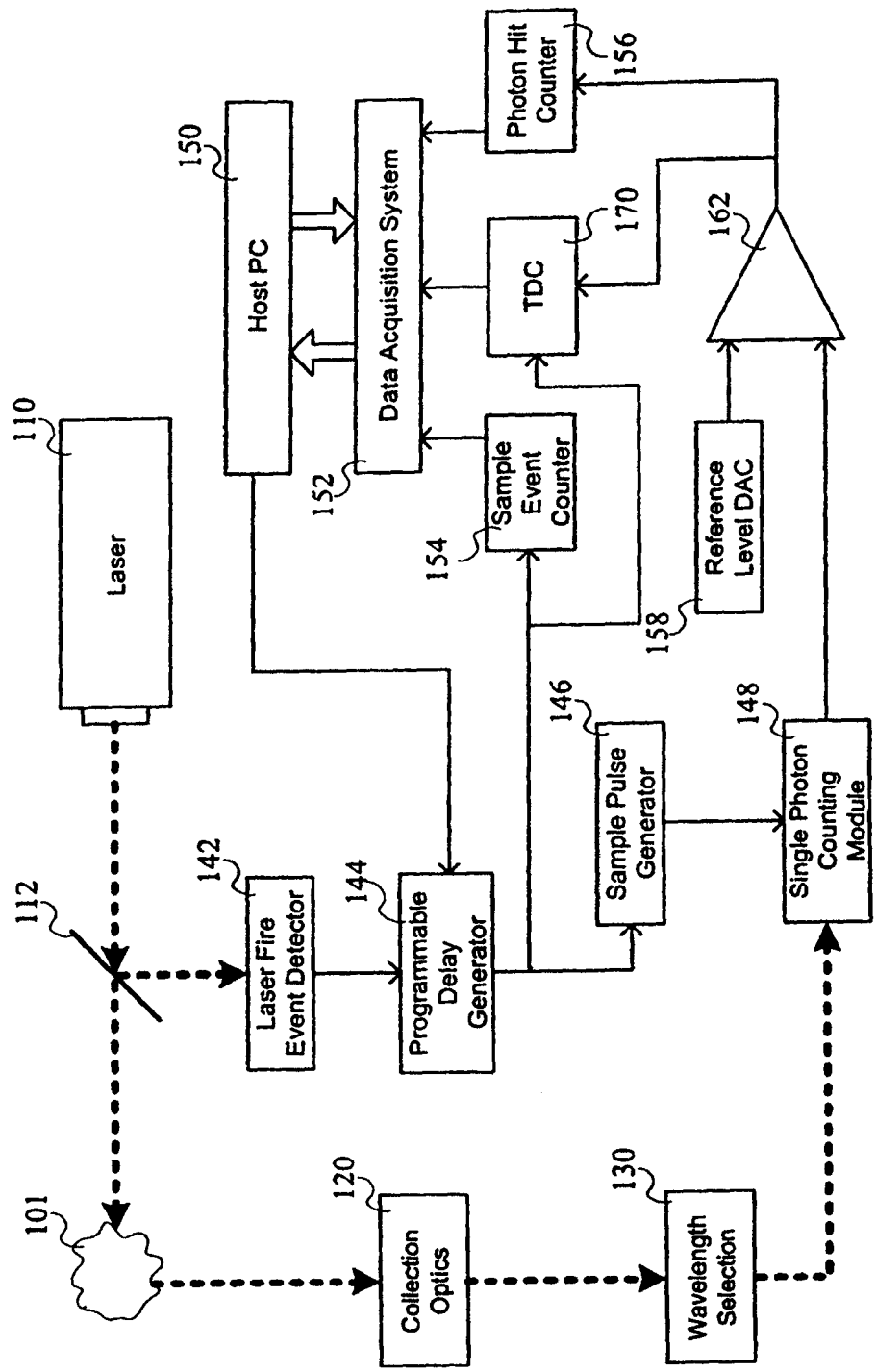
FIG. 3 depicts another time-correlated single photon counting system that provides enhanced time resolution.

FIG. 3 depicts a system configured to resolve the time of arrival of photons within the width of the sample pulse generator. Similar to FIG. 2, the laser fire event is counted by sample event counter 154. It is also used to establish the beginning of a pulse presented to a Time to Digital (TDC) converter 170. The end of the TDC pulse is preferably determined by the exact instant that the SPCM 148 detects a photon hit. The function of the TDC 170 is to convert the pulse width into a numerical value. Depending on the resolution of the TDC 170, a significantly greater time resolution may be sensed by the TDC 170 when compared with the resolution of the system depicted in FIG. 2. As a further advantage of the incorporation of the TDC 170, the increased time resolution provided by the TDC 170 does not require proportionately smaller step sizes for the programmable delay generator 144. The programmable delay generator 144 need only step in sizes equal to the sample pulse generator pulse width (typically 1 ns in duration).

As an example, given a TDC 170 with a time resolution of 60 ps and a sample pulse generator 146 with a sample of 1 ns, over 17 time-of-arrival bins within the 1 ns sample pulse interval could be resolved by the TDC 170. In effect, this is a 17 times improvement in resolution without the requirement of the programmable delay generator 144 scanning 17 times more time-of-arrival bins. The only requirement for this improved resolution is that either the photon density must be reduced, or the sample pulse width decreased to the degree necessary to decrease the likelihood of two closely spaced photons arriving during the same sample pulse time.

The system is configured to provide a photon distribution by programming the programmable delay generator 144 to scan across a range of delay times, preferably starting at 60 picoseconds and increasing in 60 picosecond increments for each laser pulse, to cover a desired range of photon delays. The system will cycle through the desired range of photon delays many times to allow for the extraction of very weak signals against a strong background. If each delay time is considered to be a bin, the sequential sampling of each bin and the addition of the number of photons counted in each bin over a large number of samples will allow for the construction of a histogram. Background radiation will contribute photon hits to the bins in a relatively uniform fashion, while discrete wavelengths or particular delays of interest from the target 101 will add additional photons to their corresponding bins.

Figure 4:
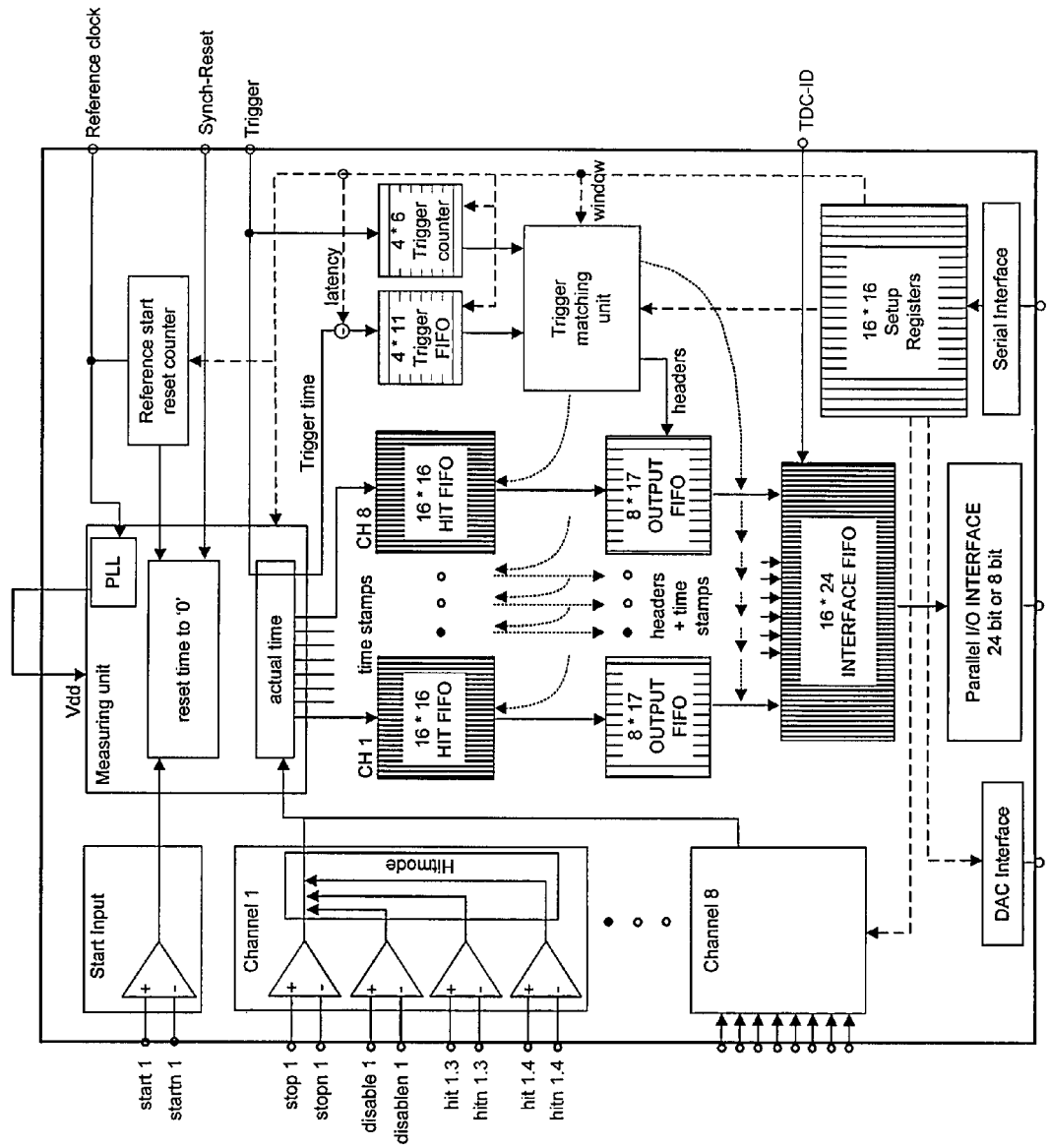
FIG. 4 (prior art) depicts a time-to-digital converter device.

FIG. 3 depicts a time-correlated single photon counting system that provides enhanced time resolution. As shown in FIG. 3, the Time-to-Digital Converter (TDC) 170 is connected to the output of the amplifier 162 that indicates a photon hit. The TDC is a device that converts small time intervals to digital values at a high resolution. Such a device can typically be provided in a single integrated circuit. FIG. 4 (prior art) depicts a TDC device, TDC-F1, available from Acam-Messelectronic Gmbh of Stutensee-Blankenloch, Germany. The TDC 170 accepts the laser fire event from the programmable delay generator 144 to establish the start of the pulse. It accepts the photon detect event from the comparator 162 to establish the end of the pulse. Once a photon detect event occurs, the TDC 170 measures the pulse width to a resolution of 60 ps, for example, and outputs it in digital form to the data acquisition system 152. Binning of photon counts to a resolution of 60 ps occurs within the host PC 150.

The system depicted in FIG. 3 detects and counts photons in the following manner. Partially-silvered mirror 112 redirects a small portion (typically 1% to 10%) of the laser 110 light pulse into the laser fire event detector 142. The event detect logic output from the laser fire event detector 142 is used to trigger the programmable delay generator 144. The Host PC 150 commands the programmable delay generator 144 to sweep between the range extents to be probed on the target 101, given that the delay time is the length of time for the photons to travel from the laser to the target and back to the system. The range extents programmed into the programmable delay generator 144 as well as the step size and number of delay steps spanning between the start and end delay settings for the programmable delay generator 144 establish the range to the target as well as the range resolution on the target. Sample event counter 154 is incremented each time the laser 110 sends an optical pulse to the target 101. As previously mentioned, not all laser pulses result in a photon detect event (typically something between 10% and 90% of laser pulses ever result in a photon detect event that can be counted by photon hit counter 156).

Preferably, the programmable delay generator 144 is programmed to sweep between a begin and end delay time in stepped intervals sufficient in number to provide the necessary resolution. For example, a target size of 5 meters located at a distance of 75 meters in a medium of air at $3 \times 10^8$ meters/sec would have a start delay of 500 nanoseconds (250 ns to arrive at the target range and another 250 ns to return to the detector) and an end delay of 533 ns. A TDC resolution of 60 ps would yield a range resolution of 550 points on the target or about 1 sample every 9 mm across the target. Upon reaching the end delay, the delay generator cycles back to the begin delay and continues stepping in 60 ps intervals.

Preferably, the signal delay is programmed at 1 ns (1000 picosecond) intervals, that is, the delay will increase by 1 ns until the entire delay range of interest is covered and then the system will cycle back to start at just a 1 ns delay. At each of the 1 ns delays, up to 17 range bins are subresolved by the TDC. The host PC 150 preferably dwells on each 1 ns delay setting for a sufficient length of time to permit the collection of photons of sufficient number to permit their histogramming into bins to provide the desired signal to noise ratio. As in FIG. 2, the signal from the programmable delay generator 144 is counted by the sample event counter 154 and is also used to trigger the sample pulse generator 146 and trigger the begin time for TDC 170. The SPCM 148 is sampled by the sample pulse generator 146, the TDC 170 will be triggered for an end hit time in the event of a photon detect by the SPCM during the pulse sample time. In the event of a photon detect by the SPCM, the photon hit counter 156 is incremented. Thus, the 1000 ps gate interval will be divided into 17 subintervals of 60 ps lengths.

Figure 12:
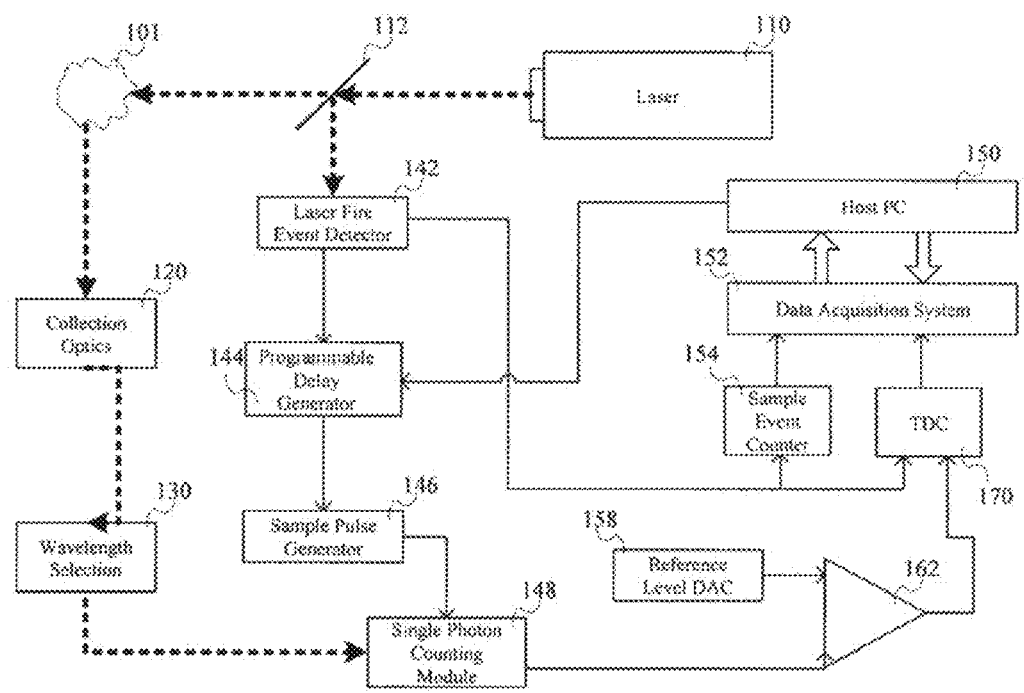
FIG. 12 depicts another time-correlated single photon counting that provides enhanced time resolution.

FIG. 12 depicts another variation of a time-correlated single photon counting system similar to that shown in FIG. 3. As shown in FIG. 12, the Laser Fire Detector 142 is used to detect the generation of a laser pulse from the Laser 110. Receipt of the laser pulse is then used to trigger the Programmable Delay Generator 144, which is programmed to generate a gate trigger signal that is delayed by selected delays from the laser pulse. The gate trigger signal is then used to the Sample Pulse Generator 146. The Sample Pulse Generator 146 provides a gate pulse with a selected duration to the Single Photon Counting Module 148 that essentially "opens up" the SPCM 146 for a selected period of time to allow it to recognize the receipt of a single photon during that period of time. The detection of a laser pulse by the Laser Fire Detector 142 is also used to trigger the Time-to-Digital Converter 170. The TDC is also triggered by the output of the amplifier 162 which is coupled to the SPCM 148. In this configuration, the TDC 170 measures the time from the detection of the laser pulse to the detection of a single photon by the SPCM. In an alternative configuration, the TDC 170 may be triggered by the output of the programmable delay generator 144, such that the TDC 170 measures the time from the start of the gate trigger signal to the detection of a single photon.

As briefly discussed above, the TDC 170 may comprise a TDC-F1, available from Acam-Messelectronic Gmbh of Stutensee-Blankenloch, Germany. A similar device, providing for time resolution up to 10 ps and total time coverage of 10 µs, is the TDC-GPX, available from Acam USA, Cincinnati, Ohio. These devices provide for highly precise time measurements to be made, allowing for highly precise determinations of photon detections to be made. Such devices also allow for the time correlated single photon counting system to be simplified by reducing the need for complex timing circuitry. The TDC 170 preferably has a time resolution of 60 ps or less, so that time histograms of photon arrivals have sufficient resolution for characterizing the target 101.

The remainder of the system depicted in FIG. 12 is similar to that depicted in FIG. 3. The event counter 154 increments each time that a pulse is generated. Pulses from the laser 110 are directed to the Laser Fire Generator 142 by an optical splitting device 112, such as a partially silvered mirror. Collection optics 120 and the wavelength selection mechanism 130 are used to collect light in the wavelengths of interest and direct them to the SPCM 148. The host PC 150 controls the programmable delay generator 144 so that the SPCM is gated on with a different delay from each laser pulse, so that the entire region of interest is covered. For example, if the gate time is 1 ns, and it is wished to cover a region of 100 ns, the host PC will command the programmable delay generator 144 to output a gate trigger signal from 0 ns to 99 ns after the detection of each laser pulse. The host PC 150 may command the programmable delay generator 144 to sequentially increment the delay by the gate time for each laser pulse to cover the region of interest and then start back at the beginning. The host PC 150 may command other delay sequences to cover the range of interest.

Gating on the SPCM 148 for a specified short period of time allows for an improvement in the signal-to-noise for photon detection by the SPCM 148. The gated on time for the SPCM 148 should be short enough so that the SPCM 148 is not overwhelmed by strong signal returns, but long enough such that the range of interest can be covered with a reasonable number of gates. If the SPCM 148 is gated with very short gates, it can be seen that a large number of laser pulses and a relatively long time will be required to cover a significant range of interest. A preferred time for gating the SPCM is 1 ns. However, longer or shorter gate times may be used.

In the configuration depicted in FIG. 12, the TDC 170 provides a elapsed time value to the host PC 150 each time a single photon is detected by the SPCM 148 and reference DC combination and output by the comparator 162. The elapsed time value is the time between the detection of a laser pulse by the Laser Fire Event Detector 142 and the detection of a photon. If a photon is not detected by the time the next laser pulse is detected, the TDC 170 simply resets and the elapsed time is based upon the detection of the next laser pulse. The host PC uses the output from the sample event counter 154 and the TDC 170 to construct a table of time delay intervals and the number of photons counted over each time delay interval for a defined period of observation. This table of time interval measurements then allows for analysis of the observed target 101.

The performance of the systems depicted in FIG. 2, 3 or 12 can be further enhanced by improving the time resolution of the gated detection process. Lasers with very short pulse widths are readily available, so the limit of how well, in time, a pulse of light can be detected may be governed by the resolution of the gated detection process. This resolution can be enhanced by using shorter time intervals over which a photon is counted.

Another approach may be to decrease the gate time of the photon detectors. As discussed above, embodiments of the system depicted in FIGS. 2, 3 and 12 use APDs for photon detection. These APDs were gated to be responsive over an interval of 1 ns. This short gate interval prevents saturation of the APD response by background and signal photons, and allows photon counting to occur. However, gating APDs over significantly shorter time periods may result in even greater background rejection and saturation prevention. Embodiments depicted in FIGS. 13 and 14 use step recovery diodes to shorten the APD sample pulse.

Rayleigh Detection Using Time-Correlated Single Photon Counting Systems

Systems using time correlated single photon counting may be used for the detection of chemical agents known as analytes. An indicator is added to the cladding material of an optical fiber which, by design, changes the optical properties of the cladding in proportion to its integrated exposure to the chemical analyte. As a result, the efficiency of light propagation through the optical fiber is a function of its integrated exposure time to the analyte as a function of concentration. Using these fibers for chemical detection purposes has involved various techniques of measuring the light propagation of a given length of fiber. Typically a stable light source is placed on one end and a sensitive light detector on the other. Measured changes in the light propagation through the fiber represent a non-point specific accumulation of exposure concentrations of the analyte over the full length of the fiber.

Optical Time Domain Reflectometry (OTDR) techniques permit position resolved measurements of analyte exposure levels at all points along the entire length of the fiber, not just accumulated over the whole fiber. For example, Chlorine detection fiber, when exposed to minute levels of Chlorine gas (Chlorine concentrations in air as small as 1 part per million (PPM)), will have its optical transmissivity reduced, causing a distributed "light leak" along the exposed length of the optical fiber. At each point along the fiber, the remaining light conducted through the fiber is inversely proportional to the spatially-cumulative, time-integrated gas exposure levels all previous points along the length of the fiber. One can measure the integrated gas exposure levels by conducting light of a known intensity into the fiber and measuring its intensity reduction profile along the length of the fiber. This requires a measurement of light intensity inside the core material of the optical fiber. This can be accomplished using a well-known property of optical fibers, Rayleigh scattering.

Rayleigh scattering is an elastic, non-absorptive process which scatters light approximately onmidirectionally. The random localized variations of the molecular positions in glass create random inhomogeneities of the refractive index that act as tiny scattering centers. Some of the Rayleigh scattered light is lost by being guided out of the cladding of the fiber into free space. The rest of the scattered light remains in the core of the fiber and is divided into two equal parts; one half scattering in the forward direction, and the other half scattering in the backward direction. Rayleigh scattered light is rather weak; typically, 532 nm light propagating in a multimode fiber will scatter a signal that is 40 to 50 db weaker than the incident light. For example, if a 1 mw optical power source is coupled to a length of fiber, a 10 nw Rayleigh signal will be scattered backward toward the source from all points along the fiber. A directional coupler separates the outgoing probe signal from the returning Rayleigh scattered signal. If the two optical signals are present on the coupler at the same time, the directionality of the coupler will limit the measurement range of the Rayleigh signal. Typically, high quality fiber optic directional couplers have a maximum directionality of about 60 dB, far less than what is needed to measure the weak Rayleigh signature. One solution is to time resolve the outgoing probe signal and returning Rayleigh signal using OTDR techniques. This results in an almost unlimited measurement range—as far as the coupler is concerned. The OTDR probe signal may be a light pulse between 600 ps and 1000 ps wide, representing a length of 10 to 15 cm in the glass core of the sensor fiber.

By sampling the Rayleigh backscattered optical power level after a variable delay from the laser fire event, one can effectively resolve the optical power level at any and all points along the length of the sensor fiber. The length of the variable delay being the time it takes the probe pulse to propagate out of the laser, through the coupler, into the sensor fiber for a distance equal to the point of interest to be measured, Rayleigh scatter from that point, propagate back through the sensor fiber, out of the sensor fiber, through the coupler, and into the sampled photodetector. To a first approximation, the measured Rayleigh backscatter optical power level, in dBm, is linearly proportional to two times the one-way optical path loss, expressed in dB. Stated equivalently, the one-way path loss to a given scattering point on the fiber is directly proportional to ½ of the measured optical power backscattered from that point. All this means is that the optical power must travel through the loss column twice; once to transport optical power from the light source to a given point on the fiber, and again to transport the backscattered optical power back through the same loss column to the light source.

A more complicated nonlinear component of the relationship between the remotely measured Rayleigh backscatter power and the actual optical power level in the sensor fiber takes into account the second order cumulative effects of all possible solutions of many-on-one backscattering. What this means is that rather than considering only one light source (i.e. the source that illuminates the fiber from its end, the backscattered light itself is now considered to be a weak light source subject to being scattered a second time somewhere else in the fiber. It is believed that secondary effects of many-on-one Rayleigh backscatter is considered insignificant for the purposes of indirect measurement of optical power levels in chemically sensing optical fibers. If one knows the Rayleigh scattering coefficient, then by measuring the absolute optical power backscattered from a given piece of fiber, one can calculate the incident absolute optical power at the point of scattering. In other words, the power levels in a given piece of fiber can be indirectly measured by measuring the backscattered light. This is, in effect a non destructive alternative to cutting the fiber to measure the optical power level.

An unexposed sensor fiber will have an intrinsic loss profile, LP(p), along its length which is representative of zero PPM gas exposure level. The intrinsic loss profile is therefore used as a reference for all subsequent Rayleigh measurements. As the fiber is exposed to its intended analyte gas, it experiences increased optical power loss at the location of the exposure when compared with that same location on the intrinsic loss profile. All subsequent exposure events will result in a cumulative, monotonic increase in the loss profile, over all exposed positions, with respect to exposure time. The loss profile, LP(p), represents the incremental change in loss as a function of position on the fiber. When one sums the loss profile over a given length of fiber, the result is the cumulative loss of that segment of fiber. Therefore, in order to calculate the instantaneous gas concentration at any given point, but still remain independent of the gas concentrations of all previous points, one must differentiate the backreflected Rayleigh backscatter with respect to distance on the fiber. The calibrated analyte concentration, as a function of position on the fiber is represented as the difference between the pre-exposure intrinsic loss profile and the newly measured loss profile.

Figure 5:
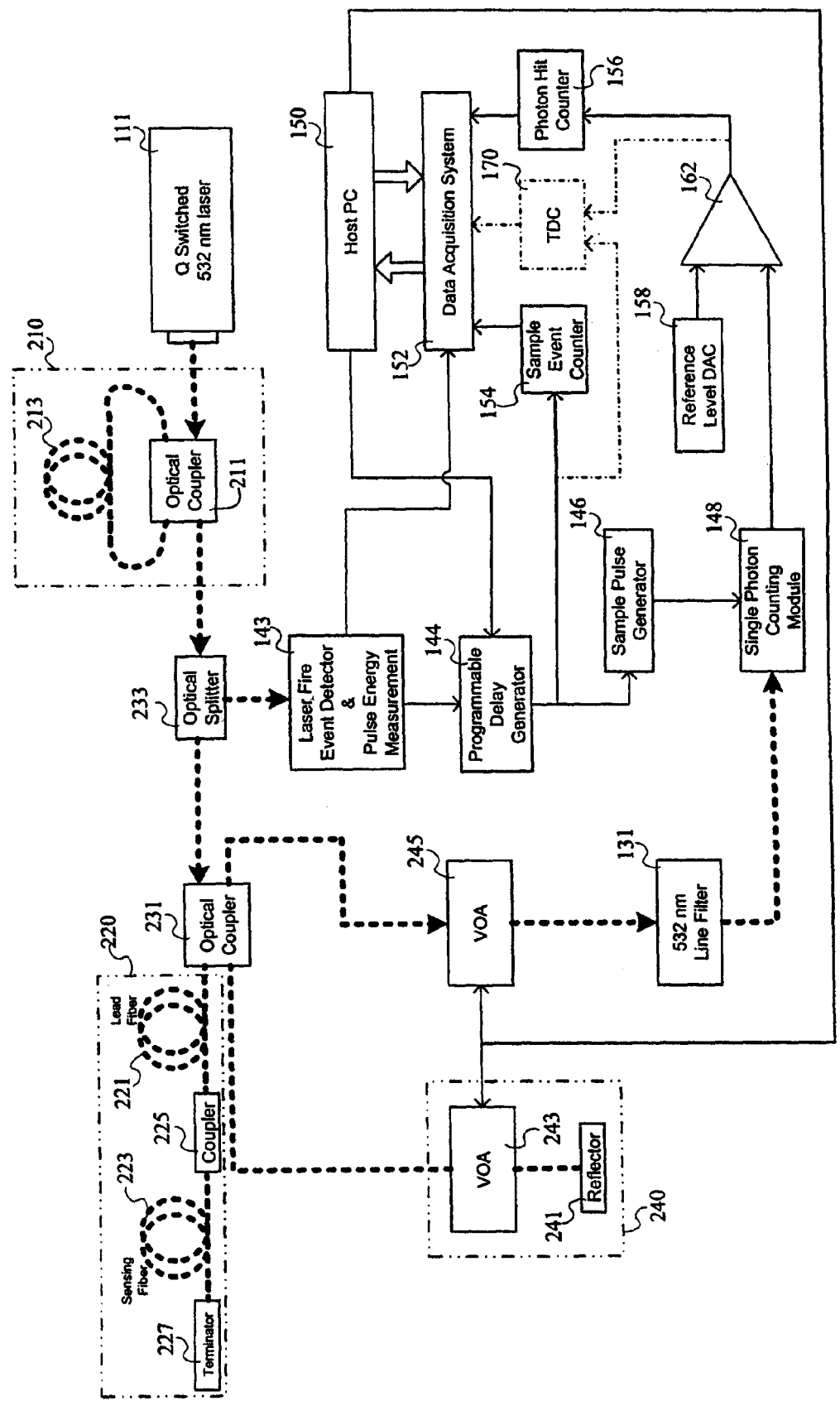
FIG. 5 depicts a time-correlated single photon counting system used to implement Optical Time Domain Reflectometry.

FIG. 5 depicts a system in which time-correlated single photon counting is used to implement Optical Time Domain Reflectometry to detect and measure Rayleigh backscatter in a chemical sensing fiber. FIG. 5 contains many element numbers that are the same as those shown in FIGS. 2 and 3. Again, the use of like element numbers in FIG. 5 indicates like elements. The discussion below addresses the elements of FIG. 5 that are not part of the embodiments shown in FIGS. 2 and 3 and also presents additional information on some of the like-numbered elements between FIG. 5 and FIGS. 2 and 3.

As shown in FIG. 5, a Q switched 532 nm laser 111 is used as a light source to fire laser pulses into an optical fiber apparatus 220 that provides for chemical sensing. The chemical sensing optical fiber apparatus 220 comprises a non-sensing lead fiber 221 and a chemical sensing fiber 223. The non-sensing lead fiber 221 is coupled to the sensing fiber 223 by a fiber coupler 225 and an optical terminator 227 is used to terminate the sensing fiber 223. Rayleigh backscatter from the sensing fiber is directed towards the SPCM 148 to generate a time profile of the Rayleigh backscatter as described below.

Preferably, a Q switched 532 nm laser is used to provide laser pulses. The laser pulses are preferably first directed into a laser comb pulse multiplier 210 comprising a low coupling ratio coupler 211 and a 1 us fiber delay 213. The multiplier 210 is capable of multiplying a 10 KHz fire rate of the DPSS passive Q switched laser by factors ranging from 10 to 100 (100 KHz to 1 MHz effective fire rate). Higher laser pulse rates increase the number of samples on the sensor fiber, which permits faster chemical detection over longer cables with greater signal to noise. These laser pulses are then sent to an optical splitter 233 with, preferably, a 99/1 splitting ratio. The output from the 1% leg of the optical splitter 233 is sent to the laser fire detector and pulse energy measurement circuit 143. The output from the 99% output leg of the optical splitter 233 launches laser pulses towards the chemical sensing optical fiber apparatus 220.

A 3 dB optical coupler 231 then serves to launch laser pulses into the chemical sensing optical fiber apparatus 220 and to couple the Rayleigh backscatter returns towards the SPCM 148. The 3 dB optical coupler 231 serves to couple as much of the light pulse from the laser 111 as possible into the optical fiber apparatus 220 to be measured. The output of the coupler 231 is connected to the optical fiber apparatus 220 to be measured. This port couples light in two directions—light from the laser 111 into the chemical sensing fiber apparatus 220, and light back-reflected from the chemical sensing fiber apparatus 220 back toward SPCM 148. As much of this back-reflected light as possible is directed into the back reflection port, which is connected to the SPCM 148, through the variable optical attenuator 245. A prime objective of the coupler 231 is to isolate the outgoing laser pulse from the incoming back-reflected light from the chemical sensing fiber apparatus 220 that is being measured by the system. The desired level of isolation is about −40 dB. This means that if the out-going laser pulse is 5000 watts peak, than 500 mW will be directed into the SPCM.

The 3 dB optical coupler 231 is also coupled to a reference and calibration apparatus 240 comprising a computer-controlled variable optical attenuator (VOA) 243 and a 100% reflector 241. This apparatus 240 connects to one of the 3 dB arms of the optical coupler 231. Input light pulses are attenuated once through the VOA 243, reflect back into the VOA 243 from the 100% reflector 241, and experience another pass thru the VOA 243 before being directed back towards the SPCM 148. A variable reference reflection that is two times the VOA setting is implemented by the reference and calibration apparatus 240. The reference and calibration apparatus 240 may be used in the system as a standard for rough calibration of back reflection measurements. Alternative embodiments of this system may not include the reference and calibration apparatus 240, or the laser comb pulse multiplier 210

The back-reflected light from the coupler 231 is directed into another computer-controlled VOA 245. The Host PC 150 constantly monitors the SPCM hit ratio (ratio of the number of photon detect events to the total number of sample intervals), adjusting the VOA 245 to maintain a hit ratio anywhere between 0.1 and 0.9. If the detection electronics in the SPCM 148 is exposed to too much light, it can saturate the SPCM, or build up charge within the APD, which may require temperature cycling to remove the built up charge. Computer control of the VOA 245 will reduce such occurrences.

Before the back-reflected light is sent to the SPCM 148, an optical bandpass filter 131 is used to filter out light at wavelengths other than that of the fundamental wavelength of the laser source 111. As shown in FIG. 5, the fundamental wavelength of the laser is 532 nm, so the line filter 131 is configured to pass light at 532 nm. Of course, if the laser 111 operates at a different frequency, the line filter 131 will be configured to pass light at that different frequency.

The laser fire detector and pulse energy measurement circuit 143 samples the high intensity laser pulse from the laser 111 to determine the energy in each laser pulse without the influence from adjacent laser pulses. This pulse energy measurement is used to renormalize the photon count samples to compensate for laser power amplitude jitter. The effect of the laser fire detector and pulse energy measurement circuit 143 is to permit less noise in the Rayleigh backscatter measurement without requiring long data collection times. This may provide for faster detection of chemical levels.

Random variations in the pulse energy of the laser 111, along with drift in the average pulse energy of the laser contribute to measurement accuracy in the final Rayleigh peak power level measured by the system, even if the SPCM 148 were perfectly noiseless. The random component of the light source noise can be filtered out by averaging, but the drift component with time cannot be filtered out in a reasonable length of averaging. A downside of averaging to remove light source noise is that the sample rate must be very high in order to attain sufficient number of samples to remove the random component of the light source noise.

Because the probe laser noise is random, independent, and un-correlated, it could be reduced by averaging a multitude of Rayleigh samples taken at the same position on the sensor fiber. The improvement in the Rayleigh measurement with averaging rapidly reaches the point of diminishing returns. The overall response time of the sensor would be unacceptably long if averaging were implemented for this purpose. The best solution is to measure both the noisy Rayleigh signal as well as a sample of the noisy probe laser pulse energy, and scale the measured Rayleigh level with the probe laser energy sample.

Figure 6:
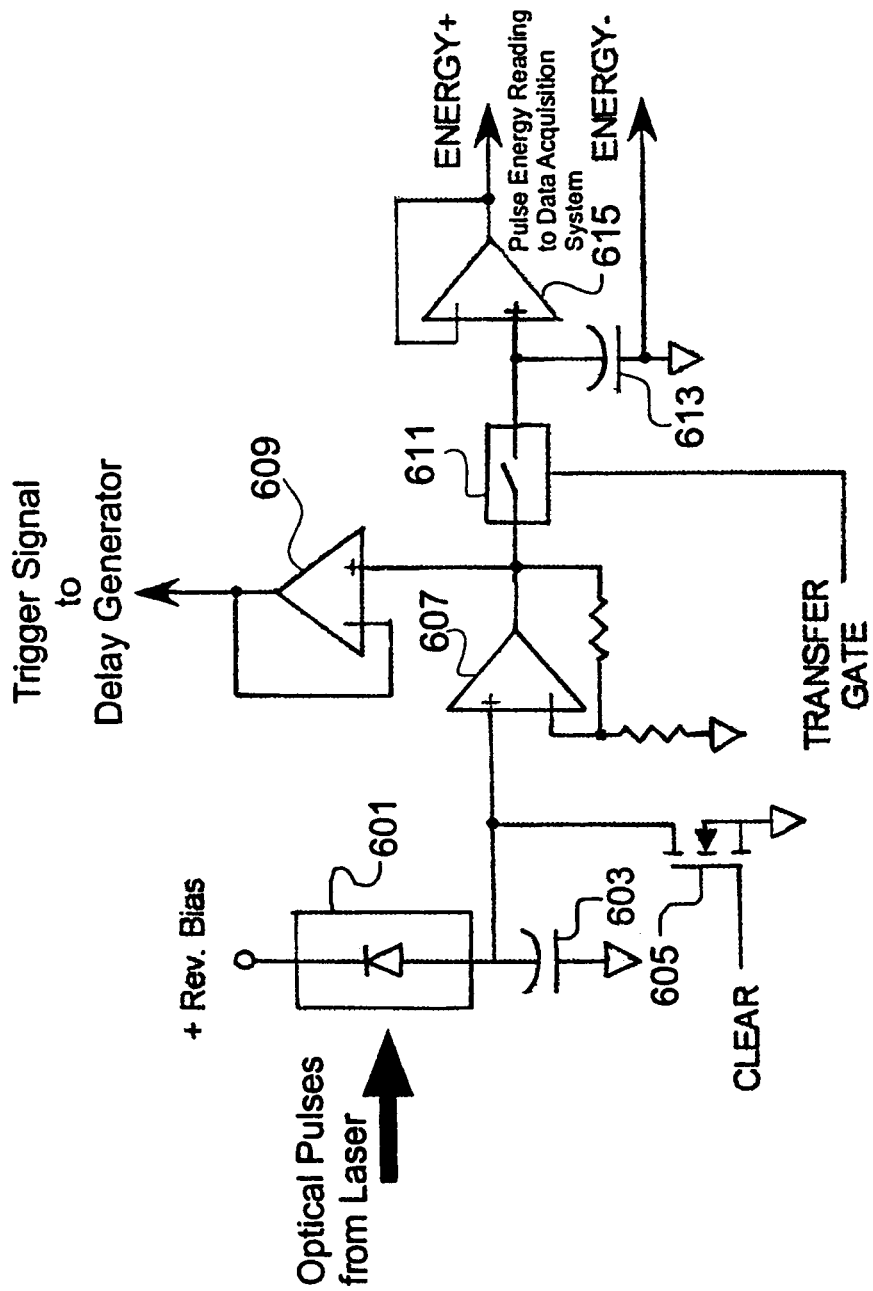
FIG. 6 depicts a laser fire detector and pulse energy measurement circuit.

As shown in FIG. 5, the probe laser pulse energy is sampled by the laser fire detector and pulse energy measurement circuit 143. This circuit 143 may comprise a high speed, small area, PIN photodiode 601 operating as a photocurrent generator as shown in FIG. 6. Since the power level of the probe laser pulse is typically very high (+23 dBm to as high as +57 dBm), the photodiode 601 itself will convert the light pulse into a current pulse which is integrated into voltage level in a capacitor 603. This voltage represents the time integral of the power profile of the laser pulse. The integral of power with time is energy, so the voltage left on the capacitor after each laser pulse is directly proportional to the total energy in the laser pulse. The voltage is inversely proportional to the value of the capacitor 603 and directly proportional to the laser pulsewidth and the peak laser power level. Even with the high peak power levels of the probe laser pulse, the capacitor 603 is preferably small to permit a 0.5 to 1 volt voltage to appear on the capacitor 603 after each pulse. For example, a 500 ps +24 dBm (250 mW) laser pulse will convert to 100 ma current pulse given the responsivity of the PIN diode 601 at 0.4 Amps/Watt. This 100 ma 500 ps current pulse is integrated into 0.5 volts in a 100 pf capacitor. A MOSFET input amplifier 605 isolates and buffers the capacitor voltage so that its value can be converted to digital form in one of the data acquisition channels. The typical laser fire rate is about 40 kHz. Given that the tolerable drift in the measurement be no greater than 0.01%, or 50 uv, then the leakage current allocation to the circuitry around the capacitor should be no greater than 200 pa. Key contributors to this leakage current are the MOSFET buffer input leakage specification, photocurrent in the PIN diode 601 between laser pulses, and leakage current through the reverse biased PIN photodiode 601 due to thermal effects. In FIG. 6, MOSFET 605 is normally in a conductive state that will dissipate any charge that is conducted thru PIN photodiode 601 due to any laser pulses or ambient light that may be present. Just prior to laser pulse whose energy is to be measured arrives at photodiode 601, MOSFET 605 is turned off, permitting any light hitting photodiode 601 to be converted into a photo current. Throughout the duration of the laser pulse, the photocurrent is collected by capacitor 603 and converted into a voltage. Since the value of capacitor 603 is small, and several sources of leakage currents exist that drain off the collected charge, the voltage appearing on capacitor 603 is buffered by a high speed amplifier 607. The voltage pulse is further buffered by buffer 609 and output as a trigger to initiate the programmable delay generator. The voltage is also conducted onto capacitor 613 by transmission gate 611. Once capacitor 613 is charged than transmission gate 611 is turned off to remove any discharge and leakage paths from the accumulated charge on capacitor 611. The voltage on capacitor 611 is further buffered by high input impedance buffer 615 and sent to the data acquisition system for conversion to a digital format.

The analog signal sent to the data acquisition system from the laser fire detector and pulse energy measurement circuit 143 can be digitized to provide a value that is directly proportional to the energy in each laser pulse. If digitized with a 14-bit data acquisition channel, the pulse energy measurement consistency should be better than 120 ppm assuming 1 LSB of system noise on the measurement. The measurement of the probe laser pulse energy directly influences the gas concentration measurements because the measured pulse energy is used to scale the measured Rayleigh levels. Each time a weak, jittery and noisy Rayleigh backscatter pulse is measured, a high level power measurement is also taken of the probe laser pulse energy. The jitter corrected Rayleigh backscatter is calculated by scaling (dividing) the raw measured Rayleigh measurement with the laser power measurement.

The Single Photon Counting Module 148 preferably comprises two specialized Geiger mode silicon Avalanche Photo Diodes (APDs). The first APD is coupled to the weak light back reflected from the chemical sensing optical fiber apparatus 220 that is being scanned. The other APD is used to balance out the overpowering sample pulse to leave only the weak single photon avalanche artifact. This weak photon detect artifact is output from the SPCM 148 where it is thresholded by the reference DAC and amplifier 162. The APDs are sampled by a sample pulse from the sample pulse generator 146. The sample pulse is applied to the two identical silicon APDs, one exposed to the light to be measured and the other is masked from light. The capacitive feed-through current pulse is identical for both APDs, but the photon induced pulse will only occur for the APD which is exposed to light. The output from the two APDs is compared to yield the difference, effectively nulling the effects of the capacitive feed-through. The sample pulse generator 146 preferably comprises an avalanche sample pulse generator that generates a sample pulse greater than 150 volts and less than 1 nanosecond in duration. The sample pulse generator 146 is triggered by the Delay Generator, which may provide a current mode logic pulse of a few nanoseconds in duration.

FIG. 11A shows a schematic diagram of a sampled single photon counting module (SPCM). The sampled SPCM accepts high voltage sample pulses into SMA connector $J_2$.

50 ohm microcoax transmission line $TL_4$ carries the resultant photon detect pulses away from the SPCM and conducts them to the comparator. Variable bias source $V_{APD}$ is typically adjusted to approximately +180 VDC. Variable bias source $V_{BAL}$ is adjustable anywhere within the range of −5 to +5 VDC. $V_{APD}$ is the operating APD reverse bias source and is typically adjusted 30 volts or more below the Geiger mode reverse bias voltage specified in the data sheets for $APD_1$ and $APD_2$. In operation $APD_1$ and $APD_2$ are connected differentially. The sample pulse is also applied to $APD_1$ and $APD_2$ differentially. The light source to be measured is conducted onto the optical surface of $APD_1$, while $APD_2$ is masked from all light exposure. $V_{APD}$ is intentionally adjusted low so that even high pulses of photons focused onto $APD_1$ will not induce an avalanche. The only way a photon can be detected is to simultaneously apply a differential, high voltage fast pulse between the cathode of $APD_1$ and the anode of $APD_2$ at exactly the same instant that a photon is allowed to impact the surface of $APD_1$. Note that $V_{BAL}$ is adjusted such that $APD_2$ is never allowed to avalanche. One side effect of the application of the high voltage differential pulse to the APDs is the capacitive feedthrough current pulse conducted through the capacitive reverse bias capacitance of the two APDs. Since the two APDs are identical in geometry, and doping profiles, the capacitance vs voltage dynamic curves exactly cancel the high voltage sample pulse. After cancellation of the sample pulses, the only pulse remaining is the photon induced avalanche pulse from $APD_1$ which causes a photon hit voltage pulse to appear across 50 ohm termination resistor $R_{10}$. Resistors $R_7$ thru $R_9$ are high valued biasing resistors (i.e. 10 k ohms). Capacitors $C_6$ and $C_7$ are DC blocking capacitors, sufficient in capacitance to conduct the capacitance feedthrough current from $APD_2$ but block the bias voltages. Toroid pulse transformer $T_2$ is designed to convert the single ended high voltage sampling pulse into a floating differential pulse. A typical sampling pulse is 30 volts or more in amplitude and 1 ns in duration. The pulse transformer is 50 ohms input impedance for the single ended primary and 100 ohm differential impedance for the floating secondary. 100 ohm differential termination resistor $R_6$ is included to dampen ringing between the inductance in the secondary of the pulse transformer and the capacitance of the APDs and parasitic capacitance of the pc board and mounting of components. The sample pulse may comprise a 30V peak-to-peak pulse from a 50Ω transmission line with a rise and fall time of about 150 ps and a total pulse width of about 1 ns. The APDs may comprise Perkin-Elmer APDs with part number C30902S.

A two sided Printed Circuit Board (PCB) pictorial diagram of the SPCM schematically shown in FIG. 11A is shown in FIG. 11B. The solder side of the PCB is shown in FIG. 11B pointing up from the page. $APD_1$ and $APD_2$ are mounted on the component side (pointing into the page) of the PCB. Both the solder side and component side of the PCB have a semi-hexagonal center region where the copper has been cut out in order to reduce the capacitance between the components. Edge launched SMA Connector $J_2$ is mounted on the edge of the PCB at the top of FIG. 11B. High voltage single ended sample pulse generator is connected to $J_2$. The primary and secondary wire windings of $T_2$ are soldered directly to the pads associated with the interconnecting components in order to reduce capacitance, lead inductance as well as to balance delays in the circuit. The toroid core of $T_2$ is positioned halfway between the ground plane and the open octagonal patch, where copper has been removed, on the solder side of the PCB. The placement of components and short traces are designed to provide equal delays and balanced capacitance between the left and right side of the differential secondary of $T_2$. This is needed in order to assure that the differential high voltage sample pulse is equal, opposite, and balanced for $APD_1$ and $APD_2$. As previously stated, $APD_2$ is darkened, and $APD_1$ is exposed to the light beam of photons to be measured. The SPCM PCB with its components is sandwiched between two machined aluminum housings providing a low capacitance cavity when assembled. An FC flange mounted collimator assembly is mounted on the component side of the housing, directly aligned with $APD_1$. FC fiber cables connected to the collimator focus photons directly on the 0.5 mm detector surface of $APD_1$. The balanced 50 ohm output of the two APDs is connected to microcoax $TL_4$, which is lap soldered to the solder side of the ground plane and exits at the bottom center of FIG. 11B.

The Avalanche Photo Diode (APD) that detects the Rayleigh back scatter within the SPCM preferably measures optical levels in the sub-femtowatt range during the sampling window. It must do this a few hundred nanoseconds after being blasted by a light pulse that is more than 14 orders of magnitude higher (the 100 mw leakage pulse from a +60 dBm probe laser pulse crossing the −40 dB coupler directivity). As configured, the SPCM 148 is theoretically capable of measuring 1 attowatt ($10^{-18}$ Watt, or about four 532 nm photons per second—only two of which are detected because of the 50% quantum efficiency of Silicon at 532 nm) to a 10% accuracy in 1 minute.

Clearly, single photon detection is a requirement, but not just for the sensitivity, but for accuracy, resolution, and dynamic range. Listed below are some of the driving requirements that may dictate the choice for a detector. However, different systems may have different requirements, so the listed requirements should not be considered as all inclusive or limiting.

a) Exposure dynamic range of input light levels: +20 dBm to −143 dBm (the SPCM 148 will be exposed to these levels, however it is not required to detect all of these levels).
b) Detection dynamic range of input light levels: +7 dBm to −143 dBm (Two detection wavelengths may be required: 532 nm and 695 nm. The detector must be capable of measuring optical power levels atf both of these wavelengths.)
c) Detection wavelength: 695 nm (Ruby) and 532 nm (frequency doubled YAG) + or −10 nm. As is discussed below, the system may operate at laser light wavelengths other than 532 nm.
d) Out of band wavelength rejection: more than 30 dB. Ranging from 200 nm to 1100 nm.
e) Measurement accuracy: Detect a trend exceeding 1 ppm from baseline, using no more than 2,000 samples per second, In 3 seconds, with a confidence >5σ. This requirement may require post processing.
f) Sample rate preferably no less than 100,000 samples per second.
g) Dead zone characterization: meet (a), (b) and (e) after no less than 50 ns (10 meters of fiber delay) of exposure to (a).

The APDs preferably comprise silicon APDs operated in Geiger Mode in order to measure the extremely low light levels (quantum detection) characteristic of weak Rayleigh scattered light. When measuring optical power levels smaller than about 1 picowatt it is practical to change the method of measurement of light intensity from the continuous units of power (the rate of light energy per unit time, Joules/sec or Watts) to the discrete units of frequency (counts per unit time or quanta per unit time or photons per unit time). Light levels are measured in photons per second and detector response is measured in counts per second. In the sub-picowatt realm the performance of detectors is measured in quantum efficiency (probability that each photon is counted by the detector) rather than responsivity (amps of photocurrent produced by each watt of optical power).

APDs are capable of measuring light in both continuous units as well as quantum units. The Geiger mode of operation of the SSPD is strictly operating in the quantum regime. The distinction of operating an APD in the continuous regime or the quantum regime is determined by the reverse bias voltage. The Geiger output of the APD is a random binary signal rather than a continuous current level, hence the name "Geiger"— from the random clicks of the instrument used to measure ionizing radiation levels—the so called "Geiger counter". While properly biased in the Geiger mode, the sensitivity of the SPCM 148 is not particularly dependent on the bias voltage—to expect this would be like turning up the power supply voltage on a logic gate in an attempt to influence its output to "become more high"—its still just a one or a zero logic level regardless of its voltage. The binary output of the SPCM 148 conveys varying light levels with the density of pulses, or frequency, and not with varying amplitude levels. There is a transition region, at bias levels below the Geiger voltage, where both the amplitude and frequency are influenced by varying detected light levels. Typically, a dark current (or dark count—in the case of Geiger mode operation) is published with each APD at a given temperature and reverse bias voltage. For example, each of the C30902S silicon avalanche photo diodes manufactured by Perkin-Elmer has a unique serial number printed on the exterior of the device from which a dark count for that APD can be determined. Shown below is a table showing the dark counts for some Perkin-Elmer APDs.

temperature of the APD and offsetting the bias voltage by the thermal coefficient is not practical because of process variations from APD to APD.

One can determine if the APD bias is too high, without having to mask all light from the APD and perform a dark count to match with the data sheet. This alternative method involves increasing the APD bias incrementally and comparing the count difference at the slightly lower bias with that at the slightly higher bias. Remember that one can still perform this test with input light levels (one does not have to completely darken the APD to measurement light)—as long as the APD is exposed to a light level that is sufficiently low that the probability of the Poisson distributed photons rarely involves the detection of 2 or more in the same sample. This method is only useful for determining the upper limit of the Geiger mode APD reverse bias—another test must be performed to determine the lower limit. The photon count increase corresponding to an incremental increase in the reverse bias will maintain a more-or-less flat response with an abrupt increase in counts at the upper limit. Backing off onto the flat response region just below the abrupt change region is the upper limit optimal point to operate the APD. This abrupt change region corresponds to the tail of the Boltzmann distributed thermal carriers whose energy is sufficient to mock photoelectrons. The flat mesa region corresponds to a more-or-less fixed number of defect sites in the lattice of the APD which trap and release electrons with a decaying time constant. These trapped electrons are usually captured from previous light exposure events to the APD and released in subsequent photon detection samples. They appear as a constant background

| | | Dark Count | | | | | | |
|---|---|---|---|---|---|---|---|---|
| Ser. No. | Temp | Rev Bias | 100% Duty Cycle | Pr(Dark) per sample | Rev Bias | 100% Duty Cycle | Pr(Dark) per sample | Notes |
| Y2680 | 22° C. | 232 | 3,051 | 0.0305 | 242 | 73,600 | 0.736 | |
| Y2681 | 22° C. | 232 | 338 | 0.0034 | 242 | 71,829 | 0.718 | |
| Y2682 | 22° C. | 234 | 314 | 0.0031 | 244 | 53,725 | 0.537 | |
| Y2683 | 22° C. | 232 | 15,508 | 0.1551 | 242 | 55,384 | 0.554 | |

The temperature at which the Geiger mode reverse bias voltage is specified is important because the reverse bias voltage of Silicon APD's has a positive temperature coefficient of 293 my/° C. The threshold for triggering an avalanche in the APD is reduced with increasing bias voltage. Usually the APD bias is only high enough to allow photoelectrons (excited by the energy released by photons absorbed in the lattice of the APD) to trigger an avalanche event. This means that for every degree Celsius that the APD is cooled, its reverse bias voltage must be decreased by 293 millivolts in order to maintain the same operating point. Maintaining a consistent temperature on the APD goes a long way toward maintaining the optimal Geiger mode bias voltage. The dark count tends to "wash out" the sensitivity of the detector for very weak optical power levels. If the APD is operating at a given temperature, and its bias voltage has been temperature corrected for Geiger mode operation, the dark count will decrease with decreasing temperature. It is desirable to reduce the dark current as much as possible by cooling the APD. This is why it is desirable to cool the APD to the lowest temperature possible, while always maintaining a stable temperature and offsetting the bias voltage for the positive temperature coefficient. The data sheet shipped with each APD only details the dark current for Geiger mode operation at a room temperature of 25° C. Therefore, simply measuring the count that is bias voltage independent. The release of these trapped charges is called "afterpulsing."

Stated differently, the dark count will tend to increase with increasing bias. Usually the APD bias is only high enough to allow photoelectrons (excited by the energy released by photons absorbed in the lattice of the APD) to trigger an avalanche event. Occasionally, the very highest energetic components of the thermal energy distribution in the APD lattice will have sufficient energy to trip an unwanted avalanche— mocking a photon detect event. Thermally generated avalanches of this nature are called dark counts. If uncorrected they only serve to "wash out" the optical signal being measured with a random uncorrelated signal. This is indicated with upward bending, away from linearity, in the lower end of the transfer function of optical power stimulus vs detector output response. The input light level is low enough that the probability of 2 or more photons triggering an avalanche event is negligible.

If uncorrected, dark counts limit the low end of the detector range, making these measurements read higher than they really are. If the dark counts are corrected, the low end of the detection range is restored. So, whenever the detector output count is disproportionately high at the low ranges, the APD bias must be adjusted lower. Maintaining a linear relationship at the low end of the detector range is accomplished by adjusting the APD reverse bias as high as possible without causing nonlinearity at the low end of the detector range.

On the other end of the scale, how does one know if the APD reverse bias is too low? If the bias is sufficiently low, the APD switches out of its Geiger mode quantum regime and into the continuous regime. Even if the bias is above the continuous regime, it is possible for the bias to be sufficiently high to permit operation in the transition regime midway between the quantum regime and the continuous regime, but still too low to operate exclusively in the quantum regime. Operation in this transition regime is unsatisfactory because the APD reverse bias is insufficient to permit single photoelectron avalanche events—in fact when operating in this regime it usually takes more than one photoelectron to trigger an avalanche event. Remember the Poisson requirement previously stated—one photon per avalanche event. When it takes two or more photons to trigger an avalanche event, the SSPD count vs input light level has a downward bending from its linear relationship.

In summary, the optimum bias for an APD is attained as follows:
a) Maintain the bias voltage as high as possible in order to maintain linearity in the probability of an avalanche vs input light level at low input levels less than −76 dBm. Evidence that the bias is too high is an upward bending in the optical response.
b) Evidence that the bias is too low is the diminished response of the SPCM. The slope of the Pr(photon hit) vs input optical power level must be maximized with increased bias within the constraint of item (a) above. Further evidence of operating with too low APD bias is the need to increase the optical power level to values higher then −73 dBm in order to achieve hits/sample of 0.1 and greater. When operating at these high optical power levels, the Poisson requirement of 1 photon per sample is violated and the response deviates from linearity.
c) Track dark count dependence on APD bias voltage. Continuously measure dark count at a given temperature and compare it with a reference dark count. If the measured dark count is lower than the reference, than increase the APD bias. If the measured dark current is higher than the reference, than decrease the bias voltage. At all times maintain a constant dark count density—that which is published with the APD in the given operating temperature. Treat the dark count as an operating point for the APD while operating in the Geiger mode. A dark count control loop may be implemented in a time division multiplexed manner (i.e. interleaved with measurement of varying light levels). This control loop can consist of collecting photon count samples when the APD is dark (for example triggering the SSPD but not the light source). This control loop shall have slow moving dynamics, and can be implemented between actual photon count measurements (i.e. real light measurements taken with the light source is really triggered).

If the APD bias voltage drops below what is necessary to maintain Geiger mode operation, the output of the SPCM is converted from a binary output to an analog photocurrent output. On the other hand, if the APD bias voltage is too high for Geiger mode operation, a marked increase in dark counts will be experienced. Continuing to increase the APD bias will increase the dark counts exponentially until the APD latches up. Preferably, special current limiting circuitry is provided in all cases (Geiger or photocurrent modes of operation) to protect the APD against over-current as a result of latch-up. Preferably, the APD in the SPCM is always operated in the Geiger mode and not in the photocurrent mode. The optimum operating voltage for the APD operating in Geiger mode is highly temperature dependent. Even slight temperature variations (e.g. $1/10$'ths of a degree C.) may have significant influence on the optimum APD operating bias that is necessary to maintain a constant overall quantum efficiency. Thus, if the APD temperature is allowed to drift, the bias supply for the APD should compensate to maintain measurement accuracy of the weak Rayleigh backscatter optical power levels. As the APD temperature decreases, the bias voltage necessary to maintain a constant level of performance also decreases. Simultaneously, the dark count must also maintain a constant performance level. The dark count level is unique to each APD. Furthermore, the dark count, given that all other conditions are equal, will decrease with decreasing temperature. However the sampled SPCM does not exhibit a significant increase of dark count with temperature, probably due to the extremely short sample pulse interval. This is because Boltzmann distributed thermal phonons with sufficient energy to mock a photo generated carrier are random and uncorrelated with the sample pulse. The sample pulse would have to occur exactly at the instant that a random phonon, with sufficient energy, otherwise the phonon would not be manifest as a dark count.

As stated above, if the APD reverse bias is too high, the APD begins to experience high dark current levels (now called dark counts when operating in quantum mode). Dark current, or counts, is caused when thermally generated charge carriers are sufficient in number and magnitude to generate an avalanche event. A thermally generated avalanche is indistinguishable from a real photon generated avalanche. The lower the temperature of the APD, the less thermal energy there is in the lattice of the APD semiconductor material, and the lower the dark current. Typically dark current is so low that it is measured in counts/sec. The effect of dark current is to limit the ultimate sensitivity of the SPCM with statistically random noise which is uncorrelated with the optical signal being measured. Because dark current is thermally generated and not optically generated, it can be measured by simply blanking the probe laser pulse and taking a sample at any random time from the SPCM. Excessive APD bias voltage will lower the threshold for allowing thermally generated events to manifest themselves as photon detection events.

Another error factor which may be measured in this manner is that of stray light leakage from the environment within which the instrument it operated. A sudden increase in dark current is probably caused by an operator un-connecting a sensor fiber while the instrument is running Stray light can be captured by an open fiber connector from overhead lights. If the APD current undergoes a sudden flash due to exposure to high ambient light levels, charge is sometimes trapped within the lattice of the semiconductor of the APD. Because the APD is operated at very cold temperatures, these trapped charges are very slowly released at random times, often manifesting themselves as photon detect events. Often, after being exposed to high light levels while at cold temperatures, an APD must be warmed to a high temperature and re-cooled just to un-trap the charge stuck in the lattice. Rapid dark current regulation will mitigate this problem of trapped charge. This is accomplished by constantly monitoring the dark current count. If an excessive dark count is detected, the APD bias is immediately reduced to whatever level is necessary to remove the excessive dark count. This reduced APD bias condition remains as long as necessary until the high ambient light level is removed. While in this "safe mode", all measurement activity is suspended so that the control software may constantly attempt to increase the APD bias back to normal. While in "safe mode" the control software preferably never increases the APD bias past the point where the dark count is excessive.

Figure 13:
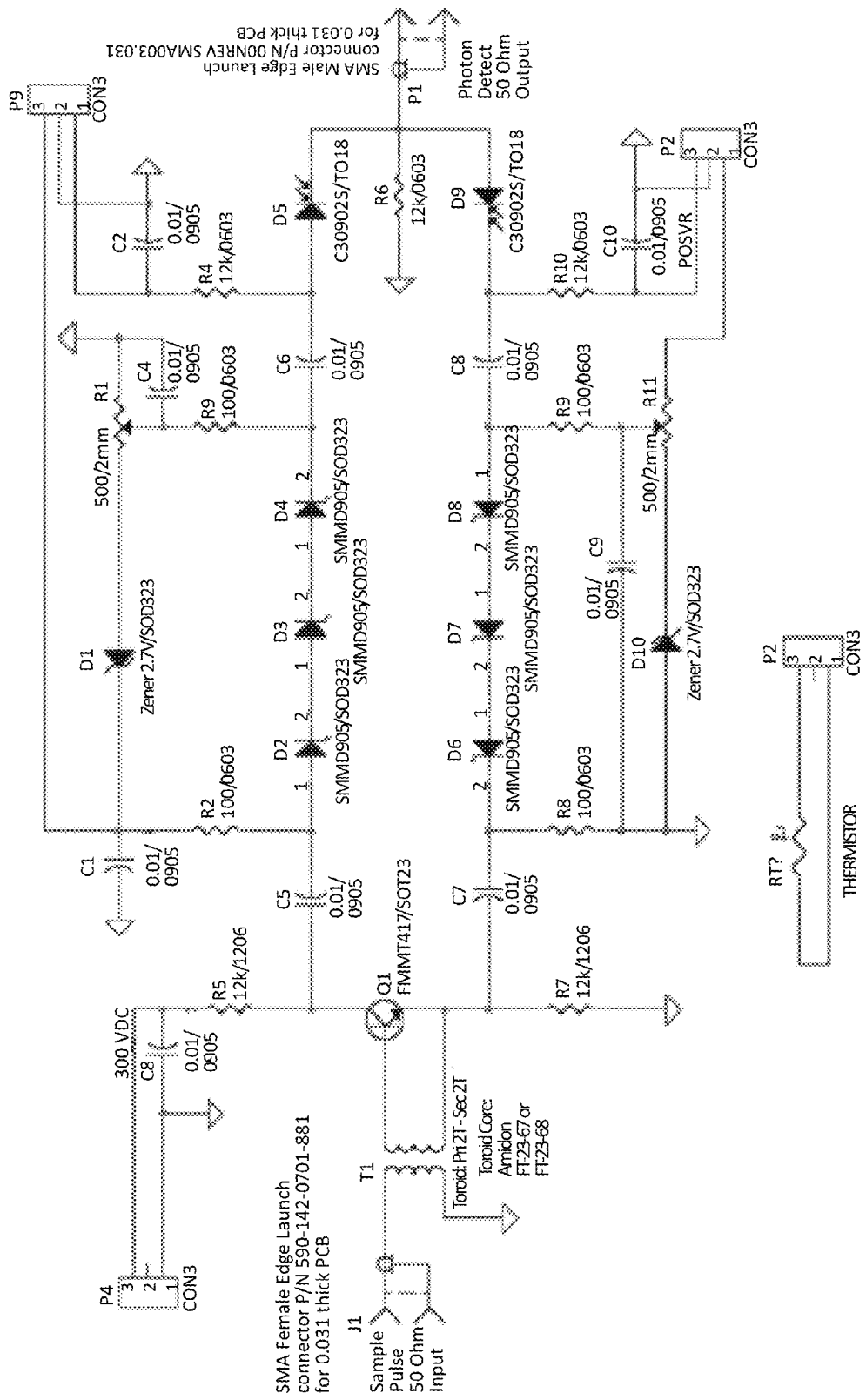
FIG. 13 shows a schematic of another single photon detector.
Figure 14A:
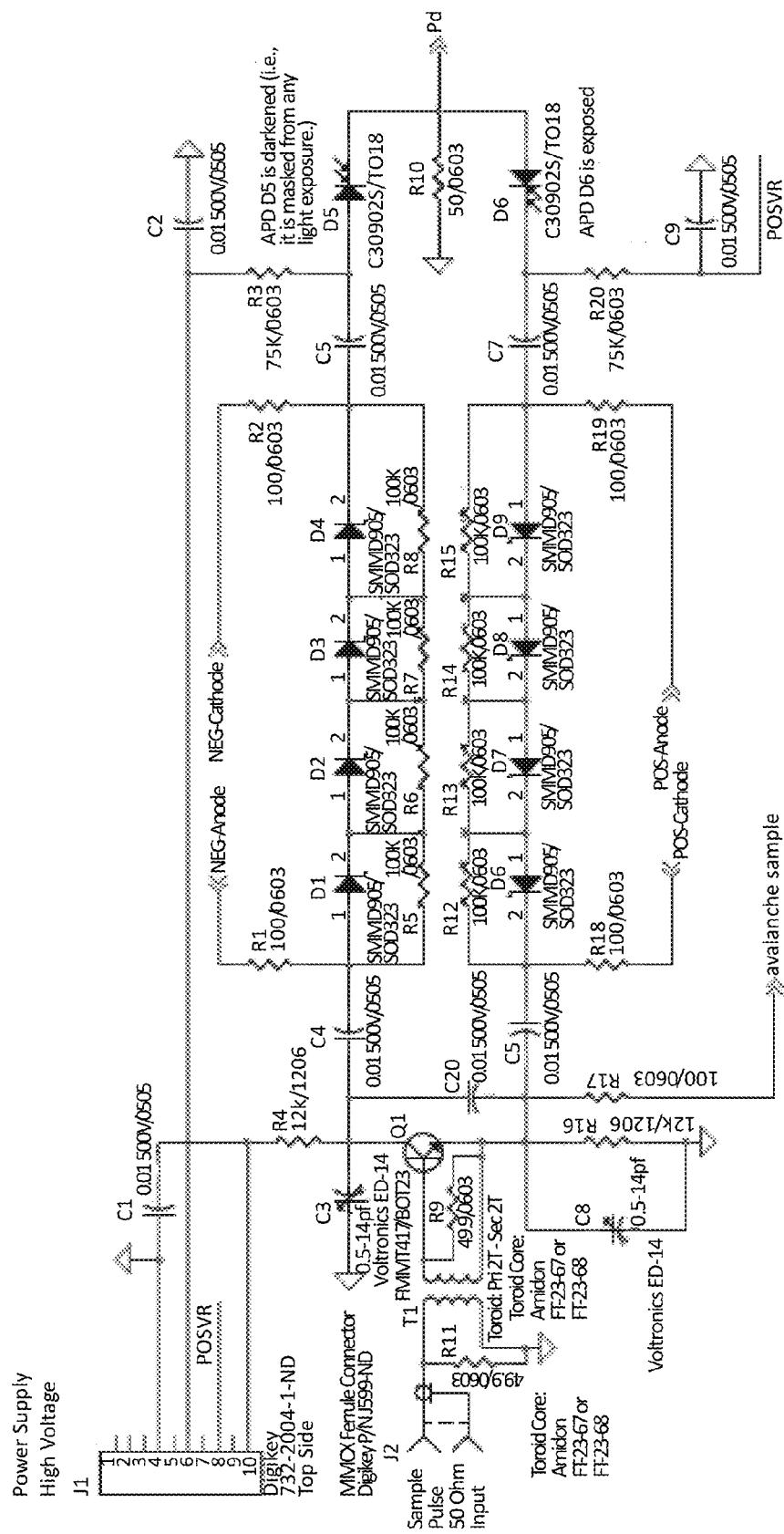
FIGS. 14A and 14B show a schematic of another single photon detector.
Figure 14B:
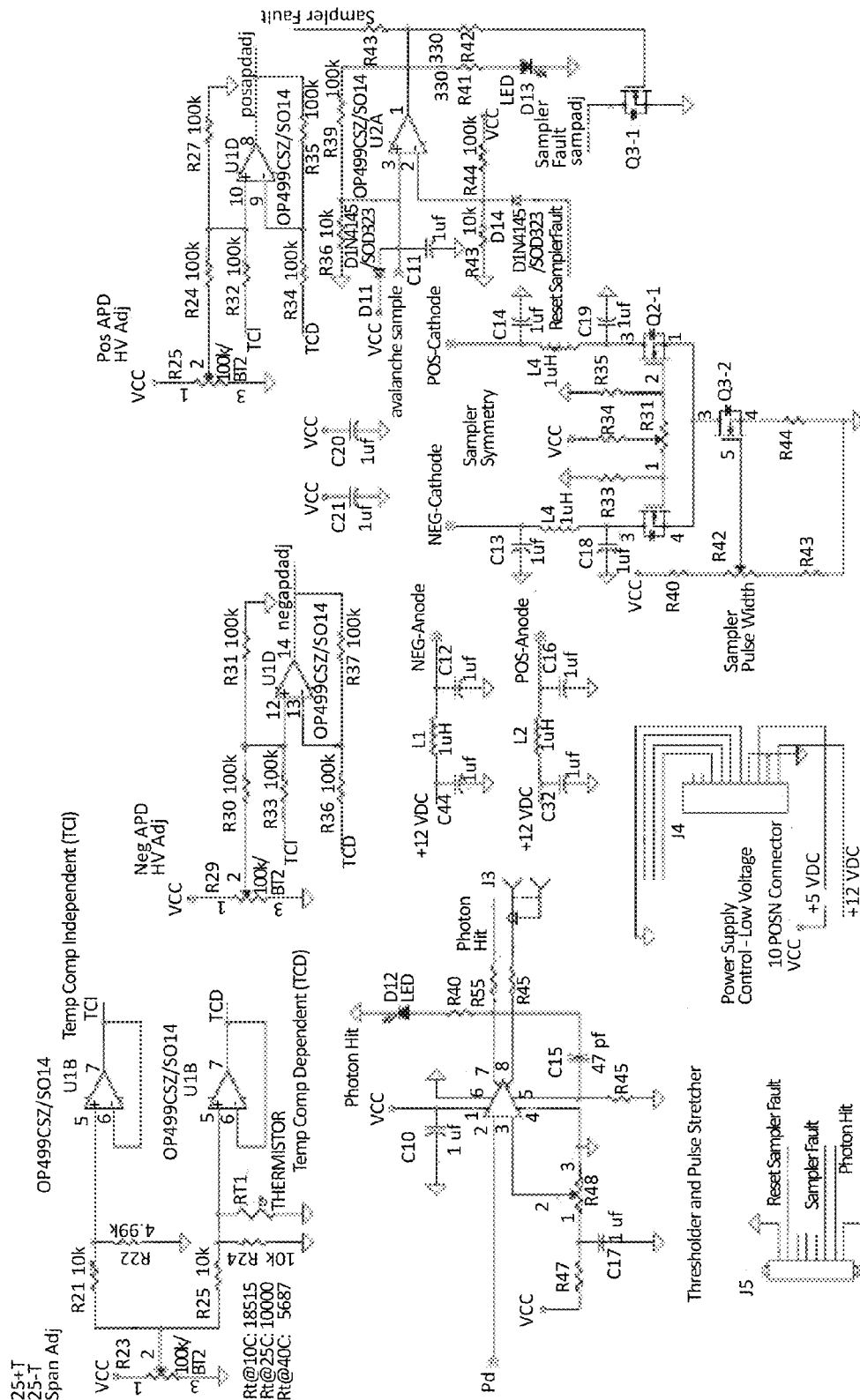

FIG. 13 shows a schematic of another sampled single photon detector circuit. The schematic in FIG. 13 shows additional circuitry over that shown in FIG. 11A. This additional circuitry implements many of the biasing and control techniques described above. FIGS. 14A and 14B show a schematic of another sampled single photon detector circuit with additional circuit changes.

As shown in FIG. 5, the SPCM 148 is preferably preceded by a Variable Optical Attenuator (VOA) 245 under control of the Host PC 150. The Host PC 150 constantly monitors the SPCM hit ratio (ratio of the number of photon detect events to the total number of sample intervals), adjusting the VOA 245 to maintain a hit ratio anywhere between 0.1 and 0.9. If the APD is exposed to too much light, it can build up charge, and require temperature cycling to remove the built up charge. Control of the APD may include a safeing feature that temporarily removes APD bias if the hit ratio is at or near unity. This tactic of folding back the APD voltage to a safe value until the high light level condition is removed, mitigates performance downtime associated with temperature cycling. If a cooled APD is allowed to operate after being exposed to high light levels, without temperature cycling, calibrated performance, as a consequence of high background noise levels may be compromised.

As indicated, it is preferred that the APDs in the SPCM 148 be operated in a temperature controlled environment. This weak photon detect artifact is output from the SSPD where it is thresholded in the analog interface board. Thermo Electric Coolers (TEC's) may be used to keep the two APD's at a preset temperature. As discussed, the lower this temperature, the lower the thermal noise floor and the more sensitive the detector. Because the APD's are capable of being maintained at temperature lower than ambient (anywhere from +60 to −40 degrees Celsius) the possibility of condensing water vapor onto the APD electronics is always present. For this reason, the SPCM may be designed so that the air can be evacuated out of an enclosure containing the APD electronics and a vacuum maintained for an indefinite length of time.

The embodiment discussed above uses silicon APDs. However, other embodiments may use InGaAs-based APDs, which are particularly useful at longer wavelengths. Silicon APDs have a greater single photon responsivity than InGaAs APDs. An obvious advantage is that 532 nm photons have almost three times greater energy when compared with 1550 nm photons. This greater energy yields a significant and decisive advantage over the sporadic energy contained in the tail of the distribution of thermal lattice vibrations. Noise in APD's, typically expressed as dark counts, occurs when an occasional phonon, or thermal lattice vibration, at the peak of its distribution, mocks a photon detect event and triggers the APD. For this reason, InGaAs APD's are cooled with thermoelectric devices to "push back" the high-end tail of the Boltzmann distributed phonons toward lower energy levels to minimize the chances of dark counts. Given the same operating temperature, silicon APD's have significantly lower noise than their InGaAs counterparts. Cooling silicon APD's, as discussed above, only improves its signal-to-noise advantage even further.

One disadvantage silicon devices have, when compared with InGaAs devices is that of their higher reverse bias voltage. At room temperature silicon APD's typically require over 200 volts of reverse bias, whereas InGaAs devices only need about 45 volts. Upon application of the high voltage sample pulse to the silicon APD, a significant amount of capacitive feed-through current is coupled thru the diode, along with the weak photocurrent from a photon detect event. A thresholding circuit must determine whether the current pulse is a photon, or capacitive feed-through, or just a thermal noise pulse. As shown in FIG. 5, the high voltage sharp sampling pulses are generated by the sample pulse generator 146. The sample pulse generator 146 may be implemented by charging a fixed length of transmission line with high voltage and dumping it into a 50 ohm load by triggering an avalanche transistor. Step recovery diodes may then be used to sharpen the edges of the sample pulse. As discussed above, the capacitive feed-through may be addressed by applying the sampling pulse to two identical silicon APD's, where one is exposed to the light to be measured and the other is masked from light. The capacitive feed-through current pulse is identical for both APD's, but the photon induced pulse will only occur for the APD which is exposed to light. The output from the two APD's is compared to yield the difference, effectively nulling the effects of the capacitive feed-through.

FIG. 5 shows the use of a Q switch 532 nm laser. However, an alternative embodiment of the system may use a pulsed diode laser. When configured for a pulsed laser diode (typically all wavebands other then 532, 808, and 1064 nm), a given amount of uncertainty is added to the measurement. The amplitude of the laser pulse can vary from pulse-to-pulse. The width of the pulse is also known to vary from pulse-to-pulse. These two sources of laser pulse uncertainty, varying amplitude and varying pulse width, result in an overall uncertainty in the laser pulse energy that is used to probe the sensor fiber. High peak pulse power levels are possible with moderate power laser diodes because the probe laser pulse is a narrow pulse, often less than 1 ns in duration. This means that one can design the laser pulse generator for very low duty cycle operation (i.e. the laser is in an off state most of the time and only pulsed on for very short intervals of time, and at a low fire rate.) One method of driving a sub-nanosecond probe laser pulse generator utilizes a technique of avalanche cascade in bipolar transistors biased near their breakdown voltage to drive a pulse forming network, and ultimately a laser diode. The peak pulse current generated in such a manner are remarkable, often exceeding 100 amps. Because the pulse width is so short, the heating effects are negligible. It is not unreasonable to drive a laser diode designed for a maximum CW current of a few tens of milliamps, with over 100 amp pulses. Although the laser efficiency drops off at these high drive levels, the peak output power is usually an order of magnitude higher than its CW rating. The avalanche driver circuits utilize impact ionization in special bipolar transistors biased near, or above, their collector-emitter breakdown voltage. When operated in this unstable state, a small trigger current injected into the based terminal of the transistor will cause a cascade of current to flow between the emitter and the collector. The trigger pulse causes electrons to rapidly accelerate across the collector-base reverse biased junction. These high velocity charge carriers acquire sufficient energy to permit their collision with neutral atoms to release additional charge carriers through impact ionization. These newly generated charge carriers are also accelerated and cause additional impacts and still further generation of charge carriers. This results in a cascade of charge carriers permitting very high currents to flow through the collector-emitter terminals of the device. The nature of the avalanche process is such that the energy of the pulse driven to the laser diode may vary somewhat with both a random and drift component.

A typical pulsed diode laser may comprise a 726 nm pulsed laser diode source. Such a laser is capable of outputting a pulse-width of about 1 to 2 ns in duration with a peak power of over 3 watts peak. Passive Q switched lasers fire at a fixed rate of 10 KHz whereas the pulsed laser diodes fire at a programmable rate ranging from tens of Hz to 100's of kHz, and in some cases even in the MHz range. Although the pulsed laser diodes do not output anywhere near the 1000's of watts of peak power of the passive Q switched lasers, they do have the ability to fire at significantly higher rates (typically many 100's of times higher rates than the passive Q switched lasers). This higher fire rate equates to more photon collection samples, and a higher confidence of chemical detection in less time. Obviously, the much lower peak output power limits the length of fiber that they can penetrate (i.e. shorter lengths of sensor).

Typical Passive Q Switched DPSS lasers have a fixed pulse rate of 10 KHz, 900 ps per pulse about 2 microJoule energy per pulse with a peak pulse power of 2,500 Watts. Such lasers may have a rather "dirty" output. The "dirty" output is a consequence of the lack of "built-in" line-pass filtering of the output spectra of such lasers. Such a laser will output at 532 nm, but a significant amount of power is also output at the fundamental of 1064 nm (about 50% of the power level at 532 nm), as well as 808 nm (about 25% of the 532 power level). The pulse-width, pulse shape, and pulse stability of the 1064 nm and 808 lines are identical to that at 532 nm. No measurable delay exists between the outputs at any of these three wavebands. By line-pass filtering the output of such a laser to one of these three lines, the system can be modified to operate at this waveband. The Silicon SPCM 148 receiver may operate at all of these wavebands, with slight responsivity differences at each waveband.

The system shown in FIG. 5 provides a time measurement for the Rayleigh back-scatter generated due to chemical exposure at some point along the sensing fiber 223 within the chemical sensing optical fiber apparatus 220. This time measurement can then be translated to a particular position within the sensing fiber 223, which then provides an indication of the exposure location of an analyte. The accuracy of the time measurement can be improved through the use of the TDC 170 as discussed above. The back-scatter response as a function of time or distance can be shown to a user through the use of a display generated by the Host PC 150.

Raman Detection Using Time-Correlated Single Photon Counting Systems

Systems incorporating time correlated single photon counting may be used for identifying trace residues of explosive materials on solid surfaces through Raman detection. For example, such a system may allow for soldier carried, or HMMWV mounted, stand-off detection of explosive residues on vehicles, buildings, and personnel, and of suspected improvised explosive devices (IEDs) that may be buried or hidden in decoy materials such as animal carcasses.

One way to identify molecules in a target is through the use of vibrational spectroscopy. It is known in the art that atoms within molecules vibrate at $10^{12}$ to $10^{14}$ Hz. Differences in quantized vibrational energy levels of molecules correspond to infrared region of EM spectrum. The set of vibrational energy levels and their differences are relatively unique signatures of a particular molecule. There are two approaches to measuring vibrational spectra to detect and identify molecules: (1) Infrared absorption/emission spectroscopy, and (2) Raman spectroscopy.

Both approaches may be implemented by illuminating a target with a light source, such that any transitions in the vibrational spectra is driven by the photons from the light source. The transitions may be manifested in two ways: dipole interactions and polarizability. With dipole interactions, the EM field of photon couples with changing dipole of molecule. The photon is absorbed to place the molecule in a higher energy vibrational state. Conversely, interaction that causes the emission of a photon will place the molecule in a lower energy vibrational state. With regard to polarizability, when the EM field of the photon couples with the changing polarizability of molecule, light is scattered. There are three scattering modes: (1) if there is no photon energy change, then Rayleigh scattering occurs (as discussed above); (2) if there is photon energy loss, then Stokes Raman scattering occurs ($v_{scat} < v_{excite}$); and (3) if there is photon energy gain, then Anti-Stokes Raman scattering occurs ($v_{scat} > v_{excite}$). Hence, Raman spectroscopy relies on the scattering of photons with changed energy states.

Raman spectroscopy may have some advantages over IR absorption/emission for the detection of explosive residues. Both IR absorption/emission and Raman yield signature spectra that are well cataloged (even though the spectra differ). However, Raman spectra can be measured readily in the presence of water and water vapor, unlike IR spectra. The Raman excitation frequency ($v_{excite}$) can be chosen over the entire range of ultraviolet to Near Infrared light.

Current implementations of Raman spectroscopy have some limitations. Raman scattering is a low probability event, i.e., Raman cross-sections are small. The typical cross-section is $10^{-30}$ cm$^2$ Sr$^{-1}$ mol$^{-1}$ (at 532 nm excite). Rayleigh scattering can interfere with detection of Raman scattering. Ambient light can also interfere with detection of Raman scattering. Background fluorescence can also interfere with detection of Raman scattering.

Typically, in Raman spectroscopy, a target is illuminated with a laser beam. Light from the illuminated spot is collected with a lens and sent through a monochromator. Wavelengths close to the laser line (due to elastic Rayleigh scattering) are filtered out and those in a certain spectral window away from the laser line are dispersed onto a detector. Spontaneous Raman scattering is typically very weak, and as a result the main difficulty of Raman spectroscopy is separating the weak inelastically scattered light from the intense Rayleigh scattered laser light. Raman spectrometers typically use holographic diffraction gratings and multiple dispersion stages to achieve a high degree of laser rejection.

Figure 7:
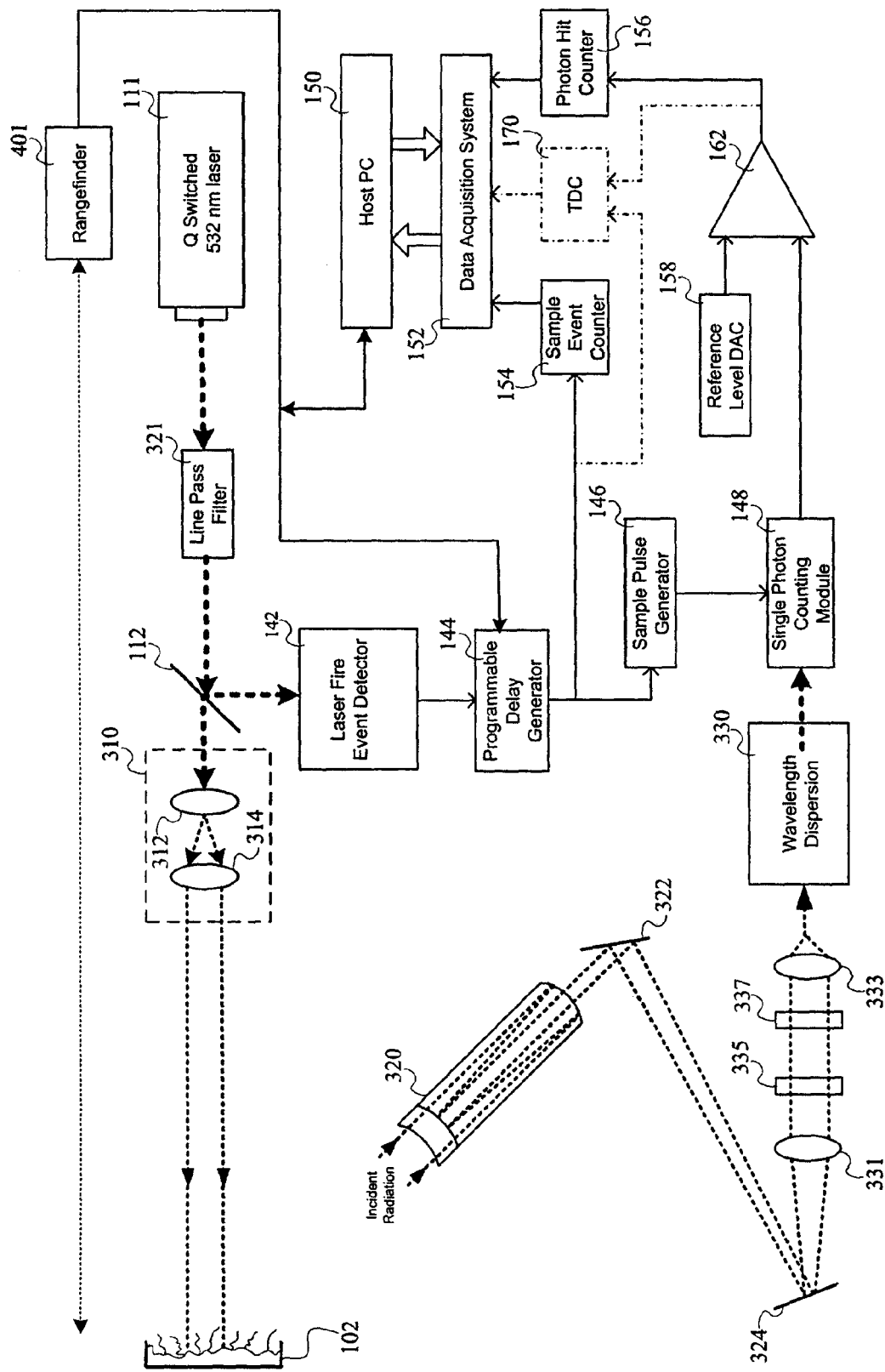
FIG. 7 shows a block diagram of a time-correlated single photon counting system that may be used for the detection of Raman scattering from a target.

FIG. 7 shows a block diagram of a system that may be used for the detection of Raman scattering from a target. Again, like numbers indicate like elements. Further, the description of like elements presented above also applies to some embodiments of the system as shown in FIG. 7. The system shown in FIG. 7 uses frequency-to-time transformation to perform Raman detection in the manner described below.

In FIG. 7, a Q switched 532 nm laser 111 launches laser pulses through a line pass filter 321 that serves to pass only the desired fundamental wavelength and suppress other wavelengths. Even though FIG. 7 shows a 532 nm laser, such a laser may significant pulses at other wavelengths, as discussed above. Therefore, the line pass filter 321 may be alternatively configured to pass laser pulses at these other wavelengths. The laser pulses are then directed towards the half-silvered mirror 112, which directs some portion of the laser pulse energy to the laser fire event detector 142. The majority of the laser pulse energy is sent to an expander/collimator 310. The expander/collimator 310 may comprise several optical lenses 321, 314 or other optical apparatus. Preferably, the expander/collimator 340 expands the laser pulses into a beam that can be considered eye-safe. The expander/collimator 340 (or other optical apparatus) direct the eye-safe laser pulses towards the target 102 from which Raman spectra is to be obtained.

Portions of the Raman scattering light from the target 102 are obtained by a large aperture telescope 320. The telescope may comprise a Maksutov-Cassegrain astronomical telescope, a Schmidt-Cassegrain telescope, or other such optical devices that allow for the Raman scattered light to be collected and somewhat focused. Optical directing devices 322, 324, such as mirrors or lenses, are used to direct the collected light to a collimating lens 331. A focusing lens 333 may be used to further focus the captured light into an optical fiber or other optical transmission media to convey the light to a wavelength dispersion apparatus 330. A holographic filter 335 and/or a bandpass filter 337 may be used between the collimating lens 331 and the focusing lens 333 to eliminate the signal at the fundamental frequency from the laser 111 and minimize background light.

Figure 8:
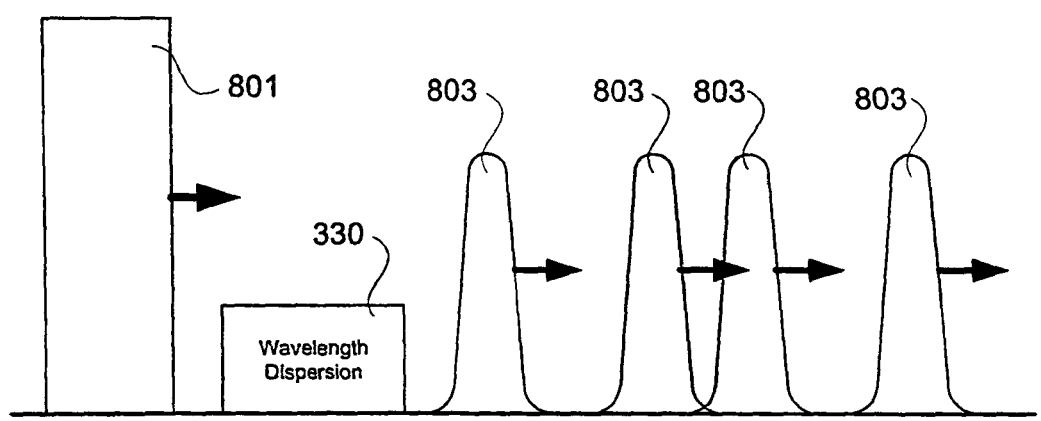
FIG. 8 shows frequency to time transformation.

The wavelength dispersion apparatus 330 performs a frequency to time transformation on the received Raman scattered light. Frequency-time transformation takes advantage of a property of light guiding materials known as wavelength dispersion. Wavelength dispersion occurs because the refractive index of transparent materials is not a constant, but rather is a function of both the material state, and of the properties of the light passing through the material. Therefore, while Raman scattering light received at the frequency-to-time transformation apparatus 330 may comprise a pulse of polychromatic light, the output of the apparatus may comprise light dispersed over time with several time dependent peaks. See, for example, FIG. 8. In FIG. 8, the input to the wavelength dispersion apparatus 330 is represented as a polychromatic light pulse 801. The output from the apparatus 330 comprises several individual peaks 803 separated in time due to chromatic dispersion. This wavelength dispersion method eliminates the need for the use of a conventional spectrometer, makes more efficient use of available scattered light, and is amenable to signal to noise enhancement via the SPCM 148 and other elements of the system shown in FIG. 7.

The wavelength dispersion apparatus 330 may comprise some length of optical fiber. In the range of wavelengths for visible Raman spectroscopy (ca. 500-600 nm), the refractive index of common communications fiber (1550 nm band) varies approximately linearly, decreasing with increasing wavelength. This means that if a short pulse of polychromatic light is inserted at one end of an optical fiber, the longer wavelengths will reach the opposite end before the shorter wavelengths. For common fused silica communications multimode fiber, the wavelength dispersion in the 500-600 nm range is 360 ps/nm for a 1-km length of fiber. This means that if a light pulse containing two light wavelengths, centered at 532 nm and 533 nm, is sent into a 1-km long fiber, the pulse will separate into two distributions with peaks that will emerge 360 ps apart. The amount of optical fiber needed to achieve these wavelength separations is quite small. A kilometer of optical fiber occupies a very small volume and weighs only about three-fourths of a pound. If the light coming out of a 1-km optical fiber can be measured with 180 ps resolution, the wavelength of the light can be determined at 0.5 nm resolution.

However, this approach can be limited by another property of optical fiber called intermodal dispersion. Intermodal dispersion occurs in multimode optical fiber because the light traveling through the fiber travels in many paths of different lengths. In some embodiments of the system light must be focused onto the end of an optical fiber. This means that when the light travels through the fiber it is reflecting off the interior of the fiber at many different angles. Each discrete angle at which the light enters the fiber constitutes a ray, and each individual ray defines a different total path length through the fiber. Graded index fiber minimizes modal dispersion, but does not eliminate it. For a 1 km communications fiber having a core diameter of 62.5 μm diameter, it was found that intermodal dispersion broadened the 500 ps laser pulse to 5 ns. For a 500 m length of 8.8 μm core diameter fiber, intermodal dispersion broadened the laser pulse to 3 ns.

Both a shorter laser pulse and significantly lower intermodal dispersion allow 0.5 nm resolution of Raman scattered light to be achieved. Preferably, 0.5 nm resolution is achieved to yield sufficient resolution of the Raman spectrum to allow reliable identification of the compound scattering the light. Lasers with much shorter pulse widths (100 ps to 10 fs) are commercially available. However, such lasers preferably have a high output power to enhance sensitivity.

To eliminate intermodal dispersion in the fiber used for chromatic dispersion, a specialized fiber that is single mode for radiation at 532 nm may be used. Such specialized fibers may be provided by photonic crystal fibers (PCFs) and photonic bandgap (PBG) fibers. Single-mode versions of PBG fibers have core diameters of about 30 μm, as compared to the typical 8.8 μm core diameter of conventional single mode fibers. This type of fiber accepts a stronger light signal and is less susceptible to misalignment. Very importantly, very high chromatic (wavelength) dispersion values can be achieved via proper fiber design. A commercial PCF manufactured has a measured dispersion as high as 380 ps/ns/km. However, PCFs can be custom designed to have dispersion values as high as several thousand ps/ns/km. A dispersion of more than 2000 ps/ns/km was recently reported. Such high dispersion values will allow the wavelength resolution of Raman scattered light using only short lengths of PCF. It is believed that a chromatic dispersion of 4000 ps/nm-km is achievable. Conventional PCFs also exhibit dispersions an order of magnitude higher than communication fibers, but the values are lower than in PBG fibers. An advantage of PCFs, however, is that they can have an enormously high numerical aperture (up to 0.7).

The use of single mode or multi mode optical fiber may still result in lower than desired signal levels, especially if the detection is located at some distance from the target under examination, as would be expected in a stand-off Raman detection system. For explosive analysis, the Raman spectra of particular explosive substances may be identified by Principal Component Analysis (PCA) and other pattern recognition methods. These methods can identify signature wavelengths of interest. Holographic filters can then be used to isolate wavelengths of interest in pulsed radiation by dispersing them in time. Holographic filters basically operate as free-space Bragg diffraction gratings.

Figure 9:
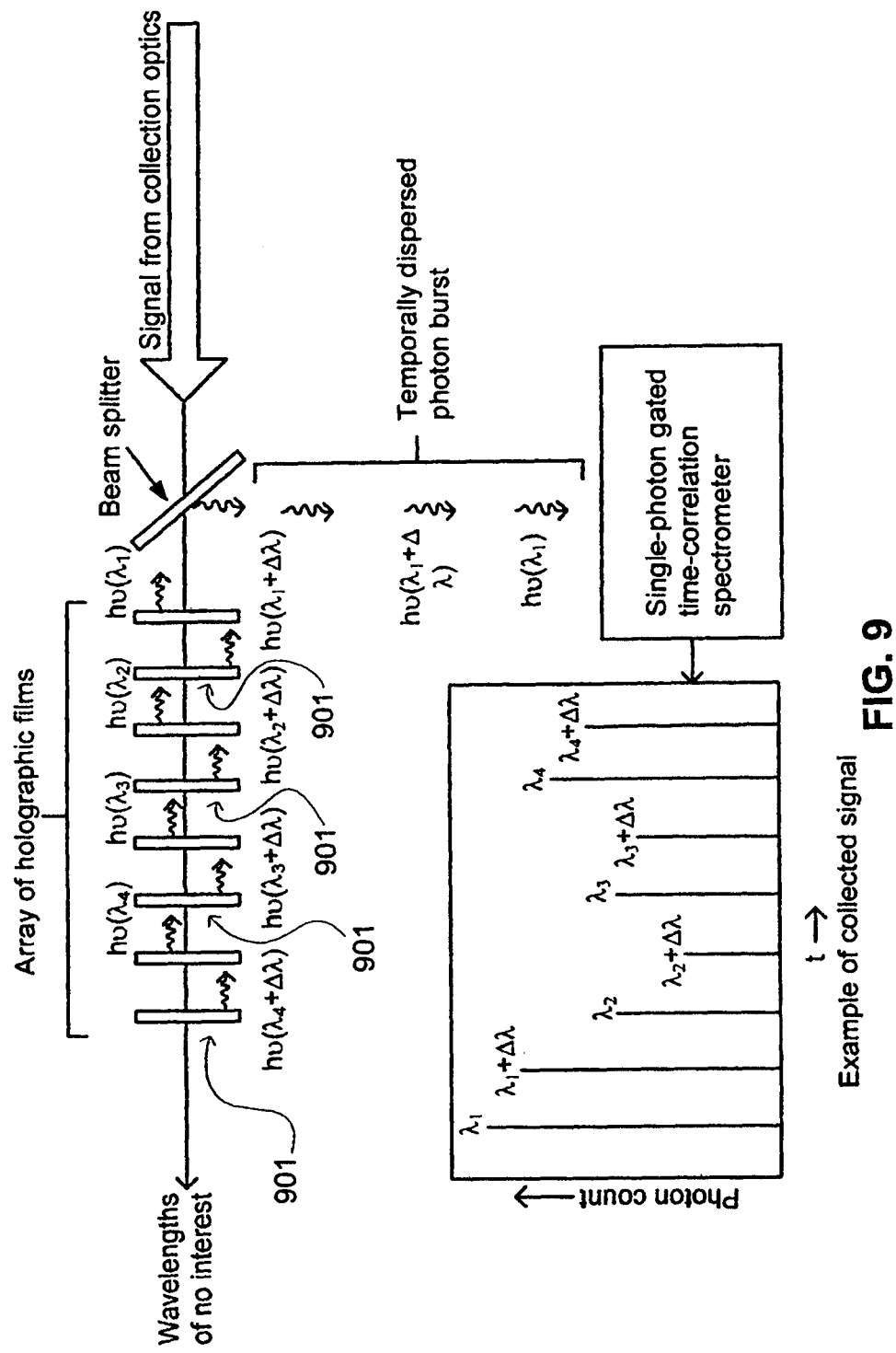
FIG. 9 shows a schematic of an optical frequency to time transformation system that uses a series of holographic filters

FIG. 9 shows a schematic of an optical frequency to time transformation system that uses a series of holographic filters 901. In FIG. 9, there are a series of holographic filters 901, each capable of reflecting a single wavelength, but passing all others. The wavelengths are preferably pre-selected using PCA or other pattern recognition methods on the basis of known libraries of spectra so that responses from threat and non-threat compounds can be distinguished. As shown in FIG. 9, there are four principle signature wavelengths $\lambda_1$-$\lambda_4$. However, there are also four additional wavelengths ($\lambda_1$+$\Delta\lambda$)-($\lambda_4$+$\Delta\lambda$), which serve as the background reference points. By spacing the holographic filters at discrete distances, the times at which photons from each reflecting filter arrive at the SPCM 148 can be adjusted to be separately counted. This design allows for the rapid accumulation of the spectra of photo responses at the signature frequencies of interest with minimal attenuation of the optical signal, and with an enhanced signal-to-noise ratio. The array of holographic filters 901 can be customized to any number of signature frequencies required for reliable classification.

Note that four wavelengths are shown in FIG. 9 for simplicity in conceptualization. In practice, the number of wavelengths is limited only by the requirements of the application.

Furthermore, it is not necessary that the holographic filters be arranged in a simple array, a matrix arrangement with multiple systems could be used for broader, multi-technique applications. Further, note that light can be coupled into the holographic filter array using simple free-space optics. This means that the overall signal strength will be orders of magnitude larger than in filter-based systems, and that alignment issues may be largely eliminated. The holographic filter array can also be easily rigidized, so that vibration and thermal effects can be compensated or eliminated.

Returning to FIG. 7, a rangefinder 401 may be used to determine the distance from the target 102 to the laser firedetector 142 and/or the telescope 320. The distance measured by the rangefinder 401 may then be used to control the programmable delay generator 144, so incrementing the delay output by the programmable delay generator 144 does not start until the Raman scattering pulse is expected to be received by the system. Thus, the rangefinder 401 may be particularly useful in a standoff system application, where the system is located some distance from the examined target 102.

The system shown in FIG. 7 provides a time measurement for the Raman scattering generated due to the exposure of the target to the laser pulses from the laser 111. As discussed, this time measurement can provide an indication of Raman spectra. The accuracy of the time measurement can be improved through the use of the TDC 170 as discussed above. The Raman scattering as a function of time can be shown to a user through the use of a display generated by the Host PC 150.

Figure 10:
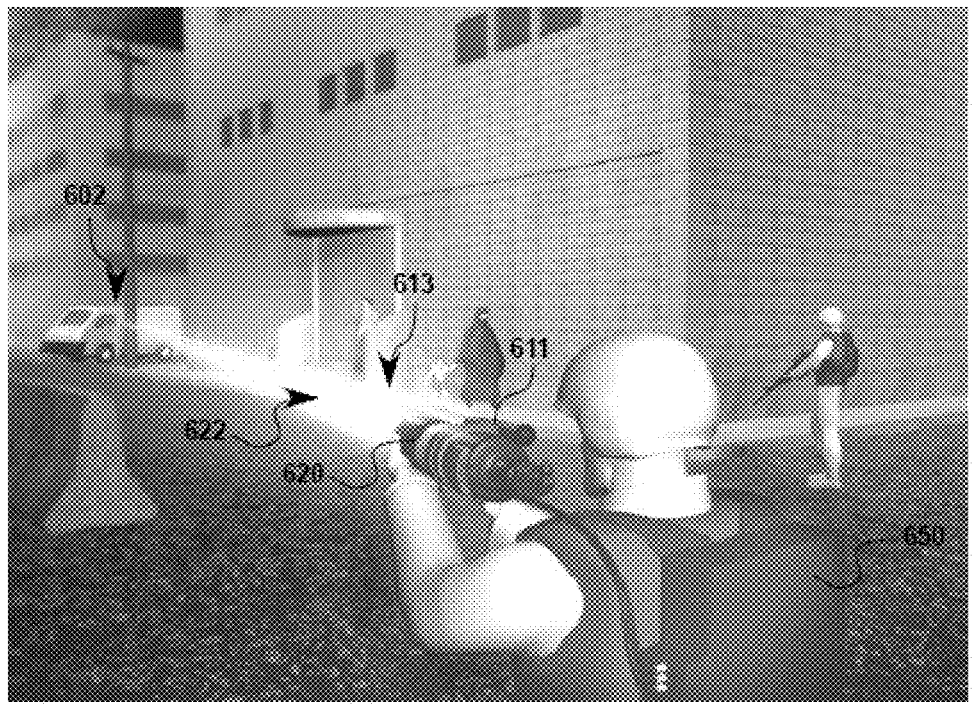
FIG. 10 illustrates an example of a standoff Raman detection system.

FIG. 10 illustrates one example of a standoff Raman detection system. The system may be a mobile system capable of being carried by a single individual. In FIG. 10, the mobile system comprises a hand-held system having a pulsed laser 611 firing a pulsed laser beam 613 towards a target 602. The return light 622 from the target 602 is captured by the telescope 620 held by the soldier. The telescope 620 may also contain the wavelength dispersion apparatus 330, SPCM 148, and other elements shown in FIG. 7. Fiberoptic, power, and data cables connect the handheld device to a backpack 650 contained a control and data analysis system. As shown in FIG. 10, the system may prove for soldier carried, or HMMWV mounted, stand-off detection of explosive residues on vehicles, buildings, and personnel, and of suspected improvised explosive devices (IEDs) that may be buried or hidden in decoy materials such as animal carcasses. Those skilled in the art will also understand that other embodiments may have applications in monitoring illegal drug activity, domestic terrorist activities, and even the illegal dumping of toxic materials. In addition, other embodiments may have use for industrial and agricultural activities, such as wide field studies of fertilizer application effectiveness, and remote analyses of trace element deficiencies in crops.

As indicated above, Principal Component Analysis (PCA) may have particular use in determining the substances detected by systems according to the present invention using single photon counting. With PCA, there may be no need to measure a complete Raman spectrum and deconvolute it in order to identify species of interest. Instead, a limited number of specific wavelengths can be emperically identified to monitor. Then, through application of PCA, the relative intensities of signal at these wavelengths can be used to determine whether key compounds of interest (explosive residue) are present.

Systems may not require the knowledge of what kind of explosive is present; it is sufficient to know that it is an explosive. This makes the application of PCA particularly useful. With PCA, all anticipated explosive compounds can be classified as those whose Raman spectral signatures fall within a limited volume in n-dimensional space. This approach can then result in decreased computational time and increased accuracy. The computation time needed to analyze the spectral data may be reduced by orders of magnitude over classical spectral analysis, thus lending the method to smaller components with less power consumption, and longer battery life in the field.

PCA is a well-established mathematical procedure that can be used to reduce the dimensionality of spectral data and to classify spectral data (i.e., classify the compounds that produced the spectra. Experimentally acquired Raman spectra may be analyzed to establish signature frequencies that can be used to identify Raman scattering that originates from explosives. For example, replica Raman spectra may be taken from different amounts of the explosives in order to determine the degree of viability that can be expected in field measurements and to devise data treatment procedures to account for such variability. The types of explosives examined may be extended to peroxide explosives, such as triacetone triperoxide (TATP), to ammonium nitrate fuel oil (amfo), and to chlorate type explosive compounds. The PCA classification algorithms and signature may then be modified to permit classification of these types of compounds as explosives even if their spectra fall in different, but distinct, regions of the PCA defined N-space.

One approach for applying PCA is described below. The first step is to collect Raman spectra for the compounds of interest (target materials) and for compounds to be excluded (non-target materials). It is understood, in the context of detection of explosives hidden on an individual or in a package, that certain common materials must be excluded from detection, these are the non-target materials. For example, the target materials may be the explosives TNT, PETN, RDX, and HMX.

The next step is to select an initial set of training frequencies. The criteria for the initial set is to select a set that are strong Raman spectra for each of the four explosives, plus a fifth that is additively strong for more than one of them. Also the selected frequencies should exclude Raman spectra for atmospheric effects, namely water. As will be appreciated, this step may have to be repeated iteratively to obtain good and possibly optimum results.

The next step is to apply PCA to the selected target frequencies to obtain a set of N-space coordinates, which may be stored. An analysis is made to determine if the N-space coordinates for the target set is sufficiently different from that of the excluded or non-target set. The goal is to find a set of frequencies in the Raman spectral range that includes spectra of all of the target materials, that after PCA provides N-space coordinates that are sufficiently different from that of the group of non-target materials, and also excludes spectra from the ambient environment, namely water such that a decision can be made that one of the explosives is or is not present.

Although it is possible that the initial frequency set will provide a useful result, it is expected that the initial frequency selected set will have to be varied in order to obtain a good result. The variation technique begins with varying a single frequency and re-running the PCA. The criteria for iterative selection of training sets is intuitive (from the perspective of a person learned in this technology) and learned based on prior results. In that repetition, frequencies should be chosen so that there is significant but not necessarily maximum Raman spectra, and for each selected signature frequency significant Raman spectra should exist for at least two compounds.

The stored N-space coordinates may be accessed and analyzed to determine whether compounds of interest cluster in a region in N-space separated from compounds of no interest. A decision is made whether or not the locations are sufficiently different. If not, the process is repeated with a new selection of frequency set. If the decision is yes, then the PCA weighting factors and N-space coordinates for the compounds of interest are output. When a set of target frequencies has been identified, the N-space coordinates and weighting factors for that set is stored to be used in field applications of the invention.

The PCA results thus obtained may then be used in an overall process for interrogating a suspected threat. As discussed above, the system shown in FIG. 7 may be used to illuminate a target and obtain Raman spectral data. The Raman spectral data obtained is analyzed to determine the intensities of the signals at different frequencies. The measured data is transformed into a threat assessment using the predetermined PCA weighting factors and N-space coordinates for the compounds of interest. This threat assessment may then be transmitted to a user.

The steps for transforming the measured data into a threat assessment may occur as follows. First, N-space coordinates from the Raman spectrum are calculated from the possible threat using the predetermined PCA weighting factors that are available from storage. This results in the measured N-space coordinates. Next the distance between the measured N-space coordinates and the predetermined N-space coordinates for the target material are calculated, where the predetermined N-space coordinates for the target materials are available from storage. Then, the uncertainty is calculated in the measured N-space coordinates along each coordinate axis. Next, statistical analysis is applied to determine the probability that the measured N-space coordinates belong to the compounds of interest. This is the threat assessment that may be communicated to the user.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. In particular it is to be understood that the disclosures are not limited to particular compositions or biological systems, which can, of course, vary. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. It is also to be understood that the terminology used herein is for the purpose of describing particular embodiments only, and is not intended to be limiting. Reference to a claim element in the singular is not intended to mean "one and only one" unless explicitly so stated. As used in this specification and the appended claims, the singular forms "a," "an," and "the" include plural referents unless the content clearly dictates otherwise. The term "several" includes two or more referents unless the content clearly dictates otherwise. Unless defined otherwise, all technical and scientific terms used herein have the same meaning as commonly understood by one of ordinary skill in the art to which the disclosure pertains.

Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . "

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A system for time-correlated photon counting comprising:
   a delay generator configured to receive a trigger signal and configured to produce a delayed electrical output, wherein the delayed electrical output is based on a programmable delay;
   an event counter configured to receive the trigger signal and configured to produce an event output for each received trigger signal;
   a photon detector configured to receive light from a light source to be measured and configured to produce a detected photon signal upon reception of a photon;
   a gate pulse generator configured to receive the delayed electrical output and configured to provide a gate pulse to the photon detector for turning on the photon detector for reception of photons during the duration of the gate pulse;
   a time to digital converter configured to produce a time interval measurement based upon elapsed time between the trigger signal and the detected photon signal; and
   a host processor configured to receive the event output and the time interval measurement and configured to produce a history of time interval measurements, and
   wherein the gate pulse has a duration less than or equal to 1 nanosecond and wherein the time to digital converter is configured to produce a time interval measurement less than or equal to 60 picoseconds.

2. The system according to claim 1, wherein the programmable delay comprises a plurality of sequentially increasing time delays with a time offset between each sequentially increasing time delay equal to a duration of the gate pulse, and the programmable delay increments from one time delay to a next time delay upon the reception of the trigger signal by the delay generator.

3. The system according to claim 1, wherein the trigger signal comprises an electrical output from a laser event detector, wherein the laser event detector produces the electrical output upon the detection of at least some portion of a laser pulse.

4. The system according to claim 1, wherein the photon detector comprises:
   a first avalanche photo diode configured to receive light from the light source to be measured and configured to produce a first avalanche photo diode electrical output; and a second avalanche photo diode masked from the light source to be measured and configured to produce a second avalanche photo diode electrical output, wherein both avalanche photo diodes are gated by the gate pulse and wherein the detected photon signal comprises a difference between the first avalanche photo diode electrical output and the second avalanche photo diode electrical output.

5. The system according to claim 1, further comprising a delay processor commanding the delay generator to produce the programmable delay, wherein the delay processor commands a sequence of programmable delays to cover a time region of interest, and wherein the delay processor commands sufficient programmable delays with a same delay time to allow a desired signal to noise ratio to be achieved.

6. The system according to claim 1, wherein the gate pulse has a selectable variable duration.

7. A system for detection of chemical agents comprising:
a laser producing laser pulses;
a chemical sensing optical fiber configured to receive at least some portion of optical energy of the laser pulses;
a laser event detector configured to receive some portion of the optical energy of the laser pulses and configured to produce a laser event detector electrical output;
a delay generator configured to receive the laser event detector electrical output and configured to produce a delayed electrical output, wherein the delayed electrical output is based on a programmable delay;
an event counter configured to receive the laser event detector electrical output and configured to produce an event output for each received laser event detector electrical output;
a photon detector configured to receive Rayleigh backscattered light from the chemical sensing fiber and configured to produce a detected photon signal upon reception of a photon;
a gate pulse generator configured to receive the delayed electrical output and configured to provide a gate pulse to the photon detector for turning on the photon detector for reception of photons during the duration of the gate pulse;
a time to digital converter configured to produce a time interval measurement based upon elapsed time between the laser event detector electrical output and the detected photon signal; and
a host processor configured to receive the event output and the time interval measurement and configured to produce a history of time interval measurements, whereby the history of time interval measurements correlates with the presence or absence of chemical agents at locations along the chemical sensing fiber.

8. The system according to claim 7, wherein the programmable delay comprises a plurality of sequentially increasing time delays with a time offset between each sequentially increasing time delay equal to a duration of the gate pulse, and the programmable delay increments from one time delay to a next time delay upon the reception of the laser event detector electrical output by the delay generator.

9. The system according to claim 7, wherein the laser event detector measures the energy of the laser pulses and provides the energy measurements to the host processor.

10. The system according to claim 7, wherein a variable optical attenuator controls the amount of optical energy directed to the photon detector.

11. The system according to claim 7, wherein the photon detector comprises:

a first avalanche photo diode configured to receive the Rayleigh backscattered light and configured to produce a first avalanche photo diode electrical output; and
a second avalanche photo diode masked from any light and configured to produce a second avalanche photo diode electrical output,
wherein both avalanche photo diodes are gated by the gate pulse and wherein the detected photon signal comprises a difference between the first avalanche photo diode electrical output and the second avalanche photo diode electrical output.

12. A system for Raman detection from a target comprising:
a laser producing laser pulses;
a first optical apparatus configured to direct at least some portion of optical energy of the laser pulses towards the target;
a laser event detector configured to receive some portion of optical energy of the laser pulses and configured to produce a laser event detector electrical output;
a wavelength dispersion apparatus having an input and an output;
a second optical apparatus configured to receive some portion of Raman scattered light from the target and configured to direct the Raman scattered light to the wavelength dispersion apparatus input;
a delay generator configured to receive the laser event detector electrical output and configured to produce a delayed electrical output, wherein the delayed electrical output is based on a programmable delay;
an event counter configured to receive the laser event detector electrical output and configured to produce an event output for each received laser event detector electrical output;
a photon detector coupled to the output of the wavelength dispersion apparatus and configured to produce a detected photon signal upon reception of a photon;
a gate pulse generator configured to receive the delayed electrical output and configured to provide a gate pulse to the photon detector for turning on the photon detector for reception of photons during the duration of the gate pulse;
a time to digital converter configured to produce a time interval measurement based upon elapsed time between the laser event detector electrical output and the detected photon signal; and
a host processor configured to receive the event output and the time interval measurement and configured to produce a history of time interval measurements, whereby the history of time interval measurements correlates with a transformation of a Raman spectra to a time domain representation of the Raman spectra.

13. The system according to claim 12, wherein the programmable delay comprises a plurality of sequentially increasing time delays with a time offset between each sequentially increasing time delay equal to a duration of the gate pulse, and the programmable delay increments from one time delay to a next time delay upon the reception of the laser event detector electrical output by the delay generator.

14. The system according to claim 12, wherein the photon detector comprises:
a first avalanche photo diode configured to receive the output of the wavelength dispersion apparatus and configured to produce a first avalanche photo diode electrical output; and a second avalanche photo diode masked from any light and configured to produce a second avalanche photo diode electrical output, wherein both avalanche photo diodes are gated by the gate pulse and wherein the detected photon signal comprises a difference between the first avalanche photo diode electrical output and the second avalanche photo diode electrical output.

15. The system according to claim 12, wherein the second optical apparatus comprises a large aperture telescope, whereby the system is deployable for stand-off detection of Raman scattering from a target.

16. The system according to claim 12, wherein the wavelength dispersion apparatus comprises a series of holographic filters.

17. The system according to claim 12, wherein the wavelength dispersion apparatus comprises optical fiber consisting of at least one of the following: single mode optical fiber, multi-mode optical fiber, photonic crystal fiber, or photonic bandgap fiber.

18. The system of claim 12 wherein the wavelength dispersion element comprises a series of fiber Bragg gratings.

19. The system of claim 12 wherein the wavelength dispersion element comprises an optical spectrograph.

20. The system according to claim 12, wherein principal component analysis of the time domain representation of the Raman spectra provides identification of chemical substances.

* * * * *